(12) United States Patent
Ahn et al.

(10) Patent No.: US 7,507,802 B2
(45) Date of Patent: Mar. 24, 2009

(54) IMMUNE STIMULATING AND CONTROLLING COMPOSITION COMPRISING BACTERIAL CHROMOSOMAL DNA FRAGMENTS AND NON-TOXIC LIPOPOLYSACCHARIDES

(75) Inventors: Bo Young Ahn, Seoul (KR); Yang Je Cho, Seoul (KR); Won Il Yoo, Gyeonggi-do (KR); Sung Ho Lee, Gyeonggi-do (KR); Hye Ran Park, Seoul (KR); Dong Hyun Lee, Gyeonggi-do (KR); Na-Gyong Lee, Seoul (KR); Doo Sik Kim, Seoul (KR)

(73) Assignee: Eyegene, Inc., Seoul (KR)

( * ) Notice: Subject to any disclaimer, the term of this patent is extended or adjusted under 35 U.S.C. 154(b) by 442 days.

(21) Appl. No.: 10/515,353

(22) PCT Filed: Sep. 26, 2002

(86) PCT No.: PCT/KR02/01813

§ 371 (c)(1),
(2), (4) Date: Nov. 18, 2004

(87) PCT Pub. No.: WO2004/039413

PCT Pub. Date: May 13, 2004

(65) Prior Publication Data

US 2005/0163806 A1    Jul. 28, 2005

(30) Foreign Application Priority Data

May 22, 2002    (KR) .................... 10-2002-0028505

(51) Int. Cl.
  C07H 21/02    (2006.01)
  C07H 21/04    (2006.01)
(52) U.S. Cl. .................................. 536/23.1
(58) Field of Classification Search ............ 536/23.1
    See application file for complete search history.

(56) References Cited

U.S. PATENT DOCUMENTS

| | | | | |
|---|---|---|---|---|
| 4,454,119 | A * | 6/1984 | Fukushi | 514/53 |
| 4,818,817 | A * | 4/1989 | Shoham et al. | 536/119 |
| 4,929,604 | A | 5/1990 | Munford et al. | |
| 5,158,939 | A | 10/1992 | Takayama et al. | |
| 5,780,448 | A | 7/1998 | Davis | |
| 6,194,388 | B1 | 2/2001 | Krieg et al. | |
| 6,207,646 | B1 | 3/2001 | Krieg et al. | |
| 6,214,806 | B1 | 4/2001 | Krieg et al. | |
| 6,339,068 | B1 | 1/2002 | Krieg et al. | |
| 6,368,604 | B1 | 4/2002 | Hone et al. | |
| 6,406,705 | B1 | 6/2002 | Davis et al. | |
| 6,426,334 | B1 | 7/2002 | Agrawal et al. | |
| 6,429,199 | B1 | 8/2002 | Krieg et al. | |
| 6,653,292 | B1 | 11/2003 | Krieg et al. | |
| 6,693,086 | B1 | 2/2004 | Dow et al. | |
| 2001/0044416 | A1 | 11/2001 | McCluskie et al. | |
| 2002/0064515 | A1 | 5/2002 | Krieg et al. | |
| 2002/0164341 | A1 | 11/2002 | Davis et al. | |
| 2003/0026782 | A1 | 2/2003 | Krieg | |
| 2003/0050261 | A1 | 3/2003 | Krieg et al. | |
| 2003/0050263 | A1 | 3/2003 | Krieg et al. | |
| 2003/0091599 | A1 | 5/2003 | Davis et al. | |
| 2003/0100527 | A1 | 5/2003 | Krieg et al. | |
| 2003/0191079 | A1 | 10/2003 | Krieg et al. | |
| 2003/0212026 | A1 | 11/2003 | Krieg et al. | |
| 2003/0224010 | A1 | 12/2003 | Davis et al. | |
| 2004/0009949 | A1 | 1/2004 | Krieg | |
| 2004/0053880 | A1 | 3/2004 | Krieg | |
| 2004/0067905 | A1 | 4/2004 | Krieg | |
| 2004/0087534 | A1 | 5/2004 | Krieg et al. | |
| 2004/0087538 | A1 | 5/2004 | Krieg et al. | |
| 2004/0092472 | A1 | 5/2004 | Krieg | |
| 2004/0106568 | A1 | 6/2004 | Krieg et al. | |
| 2004/0132685 | A1 | 7/2004 | Krieg et al. | |
| 2004/0142469 | A1 | 7/2004 | Krieg et al. | |
| 2004/0143112 | A1 | 7/2004 | Krieg et al. | |
| 2004/0147468 | A1 | 7/2004 | Krieg et al. | |
| 2004/0152649 | A1 | 8/2004 | Krieg | |
| 2004/0152656 | A1 | 8/2004 | Krieg et al. | |
| 2004/0152657 | A1 | 8/2004 | Krieg et al. | |
| 2004/0162258 | A1 | 8/2004 | Krieg et al. | |

(Continued)

FOREIGN PATENT DOCUMENTS

EP        0468520        1/1992

(Continued)

OTHER PUBLICATIONS

Gao et al Bacterial DNA and Lipopolysaccharide Induce Synergistic Production of TNF-alpha Through a Post-Transcriptional Mechanism. J Immunol. 2001 166:6855-6860.*

(Continued)

*Primary Examiner*—Mark Navarro
*Assistant Examiner*—Nina A Archie
(74) *Attorney, Agent, or Firm*—Edwards Angell Palmer & Dodge LLP; Peter F. Corless

(57) ABSTRACT

The present invention relates to immune stimulating and controlling composition comprising bacterial chromosomal DNA fragments and non-toxic lipopolysachararides. The composition of the present invention can be industrially applied the effective materials for treating cancers and adjuvant.

11 Claims, 21 Drawing Sheets

U.S. PATENT DOCUMENTS

| | | |
|---|---|---|
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0186067 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |

FOREIGN PATENT DOCUMENTS

| | | | |
|---|---|---|---|
| WO | WO-87/07297 | | 12/1987 |
| WO | WO 96/02555 A1 | | 2/1996 |
| WO | WO/98/18810 | * | 5/1998 |
| WO | WO 98/51342 | | 11/1998 |
| WO | WO 02/32450 | | 4/2002 |
| WO | WO 2004/039413 | | 5/2004 |

OTHER PUBLICATIONS

Chu et al 1997 CpG Oligodeoxynucleotides Act as Adjuvants that Switch on T Helper 1 (TH1) Immunity pp. 1623-1630.*
Li et al, Vaccine 2003, 21:3319-3329.*
Weiner et al 1997 Proc. Natl. Acad. Sci. USA vol. 94 pp. 10833-10837.*
Katoaka et al (Jpn. J. Cancer Res. 1992 vol. 83 pp. 244-247.*
Whitmore et al Gene Therapy 1999 vol. 6 pp. 1867-1875.*
Heeg et al 2000 International Archives of Allergy and Immunology pp. 87-97.*
Branda et al 1996 Journal of Laboratory and Clinical Medicine pp. 115-121.*
(XP001206755) Bacterial DNA and Lipopolysaccharide Induce Synergistic Production of TNF-α Through Post-Transcriptional Mechanism Jian Jun Gao, Qiao Xue, Christoper J. Papasian, and David C. Morrison.
(XP001206756) Cutting Edge: Bacterial DNA and LPS Act in Snyergy in Inducing Nitric Oxide Production in RAW 264.7 Macrophages Jian Jun Gao et al.
(XP002331070) Lipopolysaccharide and CpG DNA synergize for tumor necrosis factor-α production through activation of NF-κB Ae-Kyung Yi et al.
Chu et al., "CpG oligodeoxynucleotides act as adjuvants that switch on T helper 1 (Th1) immunity," *J Exp Med* 186:1623-1631 (1997).
Davis et al., "CpG DNA is a ppotent enhancer of specific immunity in mice immunized with recombinant hepatitis B surface antigen," *J Immunol* 160:870-876 (1998).
Horner et al., "Immunostimulatory DNA is a potent mucosal adjuvant," *Cell Immunol* 190:77-82 (1998).
Jakob et al., "Activation of cutaneous dendritic cells by CpG-containing oligodeoxynucleotides: A role for dendritic cells in the augmentation of Th1 responses by immunostimulatory DNA," *J Immunol* 161:3042-3049 (1998).
Klinman et al., "Contribution of CpG motifs to the immunogenicity of DNA vaccines," *J Immunol* 158:3635-3639 (1997).
Krieg et al., "Sequence motifs in adenoviral DNA block immune activation by stimulatory CpG motifs," *Proc Natl Acad Sci* USA 95:12631012636 (1998).
Krieg et al., "The role of CpG dinucleotides in DNA vaccines," *Trends Microbiol* 6:23-27 (1998).
Pisetsky, D.S. "Immune activation by bacterial DNA: a new genetic code," *Immunity* 5:305-31 (1996).
Sato et al., "Immunostimulatory DNA sequences necessary for effective intradermal gene immunization," *Science* 273:352-354 (1996).
Weeratna et al., "Reduction of antigen expression from DNA vaccines by coadministered oligodeoxynucleotides," *Antisense Nucleic Acid Drug Dev* 8:351-356 (1998).

Yi and Krieg, "CpG DNA rescue from anti-IgM-induced WEHI-23I B lymphoma apoptosis via modulation of I kappa B alpha and I kappa B beta and sustained activation of nuclear factor-kappa B/c Rel," *J Immunol* 160:1240-1245 (1998).
Yi and Krieg, "Rapid induction of mitogen-activated protein kinases by immune stimulatory CpG DNA," *J Immunol* 161:4493-3397 (1998).
Bjornnson et al., "Effects of *Corynebacterium parvum* on Murine Leukaemia," *Br. J. Cancer* 38:703-708 (1978).
Boggs et al., "Characterization and modulation of immune stimulation by modified oligonucleotides," *Antisense & Nucleic Acid Drug Devel.*, 7:461-471 (1997).
Cameron et al., "Improved *Corynebacterium pseudotuberculosis* vaccine for sheep," *Onderstepoort J. Vet. Res.* 51(4):263-267.
Conti et al., "Activation of human natural killer cells by lipopolysaccharide and generation of interleukin-1 alpha, beta, tumor necrosis factor and interleukin-6. Effect of IL-1 receptor antagonist," *Immunol.* 73(4):450-456 (1991).
Cornéline et al., "Methylated CpG-Containing Plasmid Activates the Immune System," Scandinavian Journal of Immunology 59:143-15 (2004).
Cowdery et al., "Bacterial DNA induces NK cells to produce IFN-γ in vivo and increases the toxicity of lipopolysaccharides," *J. Immunol.* 156(12):4570-5 (1996).
Feltquate et al., "Effect of CpG methylation on isotype and magnitude of antibody responses to influenza hemagglutinin-expressing plasmid," *DNA and Cell Biol.* 18(9):663-670 (1999).
Filion et al., "Development of short non-CpG phosphodiester oligonucleotides as immune stimulatory agents," *Vaccine* 21:983 (2003).
Glick, "The specificity of inhibition of tumor cell viability by DNA," *Cancer Res.* 27(1):238 (1967).
Halpern et al. "Inhibition of Neoplastic Cell Growth by Autogenous DNA," *PNAS* 61:207 (1968).
Halpern et al., "Inhibition of tumor growth by administration of killed *Corynebacterium parvum*," *Nature* 212:853-854 (1966).
Kitasato, "Immunotherapy for mice bearing myeloma and EL4 leukemia," *J. Jpn. Soc. Cancer Ther.* 22(5):958-965 (1987).
Kitasato, "Experimental studies on the Amplification of anti-tumor effects using bacterial DNA-treated cancer cells, immunoactivators and interferon," *J. Jpn. Soc. Cancer Ther.* 20(6):1107-1116 (1985).
Klinman et al., "CpG motifs present in bacterial DNA rapidly induce lymphocytes to secrete interleukin 6, interleukin 12. and interferon γ," *Proc. Natl. Acad. Sci. USA* 93:2879-2883 (1996).
Krieg et al., "CpG motifs in bacterial DNA trigger direct B-cell activation," *Nature* 374546-549 (1995).
Messina et al., "Stimulation of in vitro lymphocyte proliferation by bacterial DNA," *J. Immunol.* 147:1759 (1991).
McLaughlin et al., "Synergistic activity of components of mycobacteria and mutant salmonella in cuasing regression of line-10 tumors in Guinea pigs," *Cancer Res.* 39:1766-1771 (1979).
Okamoto et al., "Experimental anticancer studies part XXXI. On the Streptococcal preparation having potent anticancer activity," *Japan J. Exp. Med.* 36(2):175-186 (1966).
Ono et al., "Inhibitory effect of a streptococcal preparation (OK-432) on the nucleic acid synthesis in tumor cells in vitro," *GANN* 64:59-69 (1973).
Petersen et al., "Adjuvant immune stimulation with *Corynebacterium parvum* during maintenance chemotherapy of acute myeloid leukemia," *Cancer Immunol. Immunother.* 16:88-92 (1983).
Qureshi et al., "Structure of the monophosphoryl lipid A miety obtained from the lipopolysaccharide of *Chlamydia trachomatis*," *J. Biol. Chem.* 272(16):10594-10600 (1997).
Tokunaga et al., "Antitumor activity of deoxyribonucleic acid fraction from *mycobacterium bovis* BCG. I. Isolation, physiochemical characterization and antitumor activity," *JNCI* 72(4):1984.
Tokunaga et al., "A synthetic single-stranded DNA, poly (dG, dC), induces interferon-alpha/beta and -gamma, augments natural killer activity, and suppresses tumor growth," *Jap. J. Cancer Res.* 79:682 (1988).
Yamamoto et al., "DNA from bacteria, but not from vertebrates, induces interferons, activates natural killer cells, and inhibits tumor growth," *Microbiol. Immunol.* 36(9):983 (1992).

Yamamoto et al., "Unique palindromic sequences in synthetic oligonucleotides are required to induce INF and augment INF-mediated natural killer activity," *J. Immunol.* 148:4072 (1992).

Yi et al., "Rapid immune activation by CpG motifs in bacterial DNA," *J. Immunol.* 157(12):5394-5402 (1996).

Yi et al., "CpG DNA rescue of murine B lymphoma cells from anti-IgM-induced growth arrest and programmed cell death is associated with increase expression of *c=myc* and *bcl-$x_L$*," *J. Immunol.* 157(11):4918-25(1996).

Yi et al., "IFN-γ promotes IL-6 and IgM secretion in response to CpG motifs in bacterial DNA and oligodeoxynucleotides," *J. Immunol.* 156(2):558-564 (1996).

Zbar et al., Immunologic approaches to the treatment of human cancer based on a Guinea pig model, *Cancer Immunol. Immunother.* 1:127-137 (1976).

Gao, Jian Jun, et al., "Bacterial DNA and Lipopolysaccharide Induce Synergistic Production of TNF-α Through a Post-Transcriptional Mechanism," The American Association of Immunologies, (2001), vol. 166, pp. 6855-6860.

Gao, Jian Jun, et al., "Cutting Edge: Bacterial DNA and LPS Act in Synergy in Inducing Nitric Oxide Production in RAW 264.7 Macrophages," Cutting Edge, vol. 163, (1999), pp. 4095-4099.

\* cited by examiner

IMMUNE STIMULATING AND CONTROLLING COMPOSITION COMPRISING BACTERIAL CHROMOSOMAL DNA FRAGMENTS AND NON-TOXIC LIPOPOLYSACCHARIDES

This application is a United States national stage application of international application no. PCT/KR2002/01813, filed Sep. 26, 2002, and claims priority to Korean application no. 2002/28505, filed May 22, 2002.

TECHNICAL FIELD

The present invention relates to immune stimulating and controlling composition comprising bacterial chromosomal DNA fragments and non-toxic lipopolysaccharides.

BACKGROUND ART

Cancer therapy developed from the 1960s has largely involved the use of surgery, radio therapeutics and chemotherapy. These treatments have shown the effect that the upward curve of cancer death rate soared up to 1973 in the U.S. becomes sluggish. However, surgery and radio therapeutics are topical treatment and so they have limitation that patients are convalescing favorably only when cancer is early blocked as local cancer. Chemotherapy is successful only if all cancer cells are completely eliminated and so chemotherapy may damage the host, normal tissue such as immune system of patients and threaten life of the old and the weak. The main purpose of immuno-therapy is to resist the cancerization by reinforcing immune surveillance. There are several trials as follows.

1) Immunological prevention; An animal of the same class was inoculated with cancer tissue to prevent homologous cancer. For example, viral leukemia of animal may be prevented using its cause virus (Morton et al. 1991, *proc. am. assoc. cancer res.* 2: 492: 494). However, this method has never been applied to a person and it is difficult to induce cellular immunity.

2) Immunotherapy;

Active Specific Immunization

This immunization is to prevent cancer cells activating specific immune cancer supervisory cells by inoculating patients with self-cancer cells or homologous cancer cells or inactivated self or iso-cancer cells regulated by X-ray irradiation or mitomycin-C. However, this method succeeded in animal experiment not in people. Recently, in order to enhance the expression of specific antigens in cancer tissue, various methods have been of attaching with Con-A or exposing hidden antigens by treating with neuramindase or of forming hybridoma with heterologous cells. However, the use of dendritic cells (Sprinzl et al, *Cancer Treat Rev.* 2001 August; 27(4): 247-55) or development of other various DNA vaccine treatments (Pantuck et al, *Int J Urol.* 2001 July; 8(7): S1-4) still have a limit in their safety and effect.

Non-Specific Immunotherapy

This immunization most spotlighted at present is used solely or with chemotherapeutic agents for treating almost all kinds of tumors. The non-specific immunotherapy means that it will not be restricted by kinds of cancer. Although various theories on its mechanism have been suggested, they are on study only it is suggested that the non-specific immunotherapy stimulate reticuloendothelial system specifically activity of lymphocytes. There is *Corynebacterium* as the chief material actually used in clinical tests. Picibanil (OK-432), which has been used for patients in Korea already, has been studied and produced mainly in Japanese pharmaceutical company. It has been marketed in Japan, Korea or Southeast Asia. Materials formed of Picibanil has been used in treating cancer long before. In 1968, Bush Fehleison et al., Germans, discovered that the progress of cancer ceased or previously existing cancer decreased. In 1891, Coley, surgeon in Chicago, the U.S., made mixed toxin formed of materials extracted from culture medium of streptococci, which was used for many patients.

BCG (or Tubercle *Bacillus*) and Associated Material Thereof

Living BCG organism: In the 1960s, Old in the U.S. and Mathe in France reported that animal cancer could be cured by inoculating BCG. In 1970, Morton in the U.S. reported that melanoma could also be cured by inoculating BCG. As a result, BCG and its associated materials were broadly used as non-specific immunotherapy. A great amount of BCG inoculation is required to expect increasing immune response. BCG can be inoculated under the skin, directly in cancer tissue region or orally administrated. However, the oral administration of BCG is not effective for people who were inoculated with BCG in their neonatal days but came into contact with tubercle *bacillus* thereafter (BCG or tubercle *bacillus* are not absorbed in people having tuberculin positive). In the treatment using living BCG organism, there are side effects such as requiring the great amount of living BCG organism and ulcer around injection, systemic symptom like chill, fever or liver function disorder. However, in case of using the small amount to decrease the side effects, the efficacy is reduced or weak.

Unmethylated CpG DNA

Mammalian DNA is different from bacterial DNA in that they have many CpG inhibitions and cytosine of CpG dinucleotide is selectively methylated. Recently, it has been recognized that CpG motifs in bacterial DNA rapidly stimulated the polyclonal B-cells and so increased IgM secretion, and stopped the progress of cell cycle by anti-IgM antibody and powerfully inhibited the induction of apoptosis to inhibit c-myc expression and made myn, blc2 and bcl-XL mRNA expression increase to protect cells from apoptosis. In other study, it was reported that CpG motifs activated directly B-cells to increase IL-6 and IL-12 secretion within a short time. Clinical test on immune adjuvants and asthmatic treatments using synthesis oligonucleotides including CpG sequences is going in progress the CPG Company in the America.

As described above, although treatments have been developed using diverse immune regulating materials, BCG and CpG among those treatments are just applied to people. Despite broad effects of BCG, it is difficult to apply a great amount of BCG or by blood injection because of its stability. In case of CpG, synthetic oligonucleotides are too expensive.

DETAILED DESCRIPTION OF THE INVENTION

Accordingly, the object of the present invention is to provide materials for inducing immune response more stable, economic, effective and specific than the conventional ones.

There is provided immune stimulating and controlling composition comprising: bacterial chromosomal DNA fragments; and non-toxic bacterial lipopolysacchrides.

It is preferable that the bacterial chromosomal DNA fragments have size ranging from 2.0 to 0.5 kb and the lipopolysaccharides have dalton ranging from 3,000 to 10,000 dalton. The bacterial DNA sequence includes not only unmodified but also modified bases like methylated base (cytosine, adenine or guanine).

It is preferable that the least amount of the bacterial chromosomal DNA fragments and the lipopolysaccharides may be mixed to show the effect of the present invention. Particularly, the present invention shows the increase of dose dependent efficacy in a mass ratio ranging from 500:1 to 1:500. In the above-described mass ratio, the present invention is non-toxic and economic.

It is preferable that the bacterial chromosomal DNA fragments and the lipopolysaccharides are mixed by shaking.

The composition of the present invention is useful for immune adjuvants or anti-cancer treatments. These effects are shown by inducing immune activation of T-helper 1 type.

It is preferable that the bacteria in the present invention is *Escherichia coli* or mycobacteria. More preferably, the bacteria is *Escherichia coli*, particularly, *E. coli* EG0021 (KCCM-10374).

In the composition of the present invention, synergy effect by CIA02 may be expected in stability, cell immune induction, synergy effect by CIA05 may be expected in immune reinforcement specifically cancer treatment.

The disclosed immune stimulating and controlling composition comprising bacterial chromosomal DNA fragments and non-toxic lipopolysaccharides will be described briefly.

The present inventors succeeded in effective production of bacterial oligonucleotides as anticancer adjuvant and development of modified lipopolysaccharides for suitable activation as anti-cancer treatments. A new immune adjuvant, CIA07, is finally obtained by combining the bacterial oligonucleotides and the lipopolysaccharides.

Generally, the combination of lipopolysaccharide and DNA shows synergy effect. Lipopolysaccharide shows various responses such as serving as independent antigen of T-cells. Here, the synergy effect may cause crucial results such as sepsis.

The present inventors obtained a strain, *E. coli* EG0021, having short carbohydrate chained lipopolysaccharide from *Escherichia coli* in healthy human intestines. They deposited the strain with No. KCCM 10374 in Korea culture center of microorganisms, KCCM, located in 361-221 Hongje-dong, Seodaemun-gu, Seoul, Korea, in May 2, 2002. They established a method of purifying lipopolysaccharide from this strain.

*E. coli* DNA, CIA02, representing-immune activation was isolated from genomic DNA of *E. coli* EG0021. The CIA02 was obtained after fragmentation of the isolated DNA and general treatment.

CIA07 was finally obtained by combination of the CIA02 and the CIA05.

PREFERRED EMBODIMENTS OF THE PRESENT INVENTION

Figure 1:
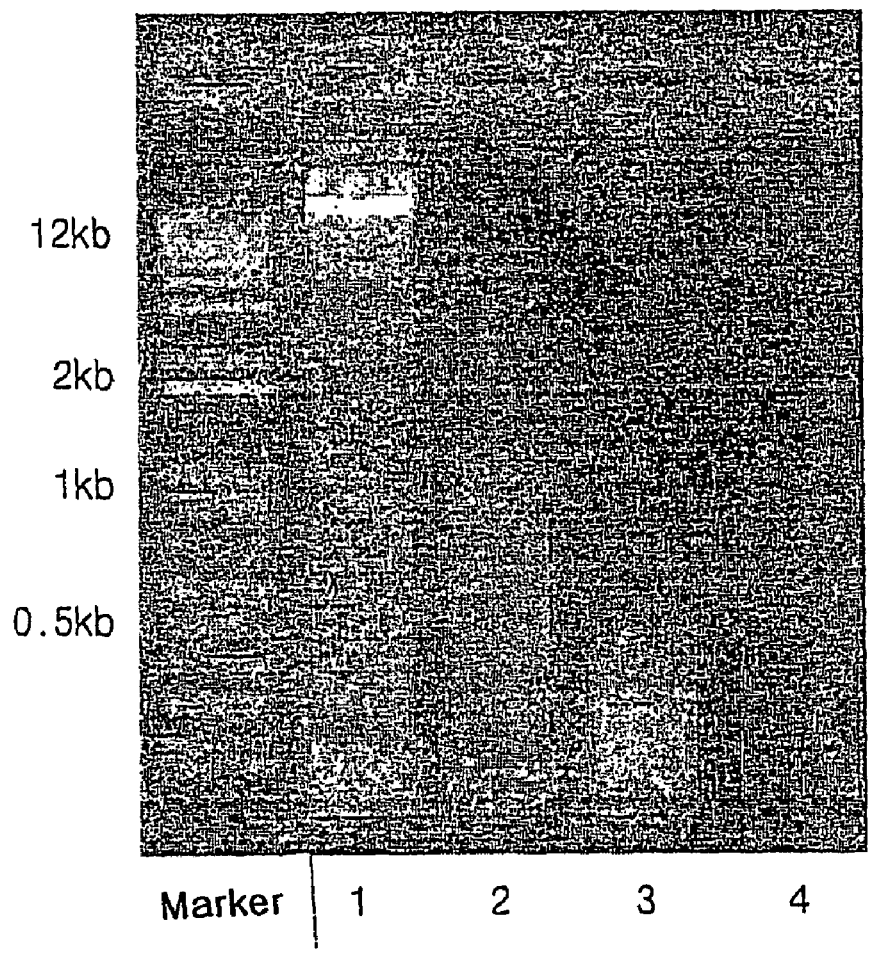
FIG. 1 is a picture illustrating *E. coli* chromosomal DNA divided into each fraction by using ultrasonicatior to detect the size of *E. coli* DNA representing the optimal effect, wherein Lane 1 represents intact, Lane 2 over 1 kb, Lane 3 2-0.5 kb and Lane 4 less 0.5 kb of DNA.

The disclosed immune stimulating and controlling composition comprising bacterial chromosomal DNA fragments and non-toxic lipopolysaccharides will be described in more details referring to examples below, when are not intended to be limiting.

EXAMPLE 1

Obtainment of Non-Toxic Strain

Screening and Isolating Mutant *E. coli* Having Short Carbohydrate Chained Lipopolysaccharide

*E. coli* EG0021 having short carbohydrate chained lipopolysaccharide was isolated from healthy human intestines, and a method of purifying lipopolysaccharide from the strain was established.

A procedure was 5 times repeated of injecting liquid-cultured single colony of *E. coli* isolated from healthy adult male intestines, into experimental animal, Balb/C mouse.

50 kinds of strains were selected therein, and one colony in the selected 50 strains was obtained from a plate. After the colony was dissolved in 4 ml of 0.9% physiological saline solution, 1 ml of the solution was moved into an eppendorf tube. The solution was treated with 2 ul of DNase I and reacted at an incubator at 37° C. for 1 hour. After treatment of DNase I, the solution was treated with 50 ul of Rnase (10 mg/ml) and reacted at an incubator of 37° C. for 1 hour. Then, 10 ul of Proteinase K(20 mg/ml) was put therein and reacted at 37° C. overnight. Human lymphocyte cell line differentiated by GM-CSF was treated with LPS of each strain obtained therefrom. TNF-α secretion was measured and a strain having the least value was selected (see Table 1) and confirmed the molecular weight of lipopolysaccharide by electrophoresis. It was shown that the attenuated strain was not morphologically changed or in its characteristics. Lipopolyaccharides having a molecular weight ranging from 5,000 to 10,000 without lipopolysaccharide ladder having a molecular weight ranging from 50,000 to 100,000 were shown in electrophoresis (see FIG. 1). This strain was called EG0021.

TABLE 1

TNF-α secretion value of E. coli homogenate obtained from healthy human intestines

| No. | TNF-a (pg/1 ul) |
|---|---|
| EG0001 | more (>100) |
| EG0002 | 12 |
| EG0003 | 72 |
| EG0004 | 85 |
| EG0005 | 25 |
| EG0006 | 35 |
| EG0007 | 71 |
| EG0008 | 28 |
| EG0009 | 2 |
| EG0010 | 13 |
| EG0011 | 39 |
| EG0012 | 64 |
| EG0013 | 8.8 |
| EG0014 | 9 |
| EG0015 | 70 |
| EG0016 | more (>100) |
| EG0017 | 6 |
| EG0018 | 11 |
| EG0019 | 0.3 |
| EG0020 | 80 |
| EG0021 | 0.1 |
| EG0022 | more (>100) |
| EG0023 | more (>100) |
| EG0024 | more (>100) |
| EG0025 | 53 |
| EG0026 | 12 |
| EG0027 | 4 |
| EG0028 | 76 |
| EG0029 | 92 |
| EG0030 | more (>100) |
| EG0031 | 21 |
| EG0032 | 1.2 |
| EG0033 | more (>100) |
| EG0034 | more (>100) |
| EG0035 | 7 |
| EG0036 | 87 |
| EG0037 | 0.7 |
| EG0038 | 39 |
| EG0039 | 37 |
| EG0040 | 91 |
| EG0041 | 65 |
| EG0042 | 54 |
| EG0043 | More (>100) |
| EG0044 | More (>100) |
| EG0045 | 17 |
| EG0046 | 2.1 |
| EG0047 | 3.5 |
| EG0048 | More (>100) |
| EG0049 | More (>100) |
| EG0050 | More (>100) |

EXAMPLE 2

E. coli DNA Preparation Method

E. coli Chromosomal DNA Purification

E. coli EG0021 was cultured by shaking in TSB (Tryptic soy broth; Difco) culture medium (30 g/L) at 37° C. for 10 hours.

After 10 L cultivation, 150 g of cells obtained by centrifugation at 8,000 G was washed in TE(10 mM Tris, pH 8.0, 25 mM EDTA) buffer solution (300 ml) and centrifuged. The cells (150 g) obtained by centrifugation was dissolved in 750 ml of lysis solution (10 mM Tris (pH 8.0), 25 mM EDTA, 100 ug/mL Lysozyme) and treated at 37° C. for 1 hour.

Thereafter, proteinase K (Sigma) was added in the solution to final concentration 100 ug/ml, and treated at 50° C. for 12 hours.

Mixing the solution with penol/chloroform/isoamyl alcohol (25:24:1) at a ratio of 1:1 was repeated three times to obtain water layer.

E. coli chromosomal DNA was obtained by ethanol precipitation.

After purified E. coli DNA was diluted using sterile distilled water, the concentration of the E. coli DNA was measured at 260 nm and 280 nms with UV spectrometer.

The concentration was measured according to the following method:

Double stranded $DNA$ concentration (ug/ml) =

$$OD260 \text{ nm} \times \text{dilution rate} \times 50$$

Single stranded $DNA$ concentration (ug/ml) =

$$OD260 \text{ nm} \times \text{dilution rate} \times 40$$

$$OD260 \text{ nm}/OD280 \text{ nm} = 1.7 \sim 1.8$$

E. coli DNA Fragmentation

The purified E. coli chromosomal DNA was dissolved in TE buffer solution to 0.5 mg/ml and sonicated in a glass beaker with ultrasonicator.

20 ml of the solution was fragmented at one time using 500 watt sonication VCX500(Sonics Co.) as ultrasonicator and 630-0220 (tip diameter: ½" (13 mm)) as tip.

Here, in order to identify the size of E. coli DNA representing the optimal: effect, the whole E. coli chromosomal DNA was divided in 20,000 J according to time period using ultrasonicator and then separated by size (see FIG. 1). E. coli DNA was divided into the whole DNA before sonication (Intact, more than 10 kb), 2.0~0.5 kb, 0.5~00.1 kb and less than 00.1 kb according to its size.

Figure 2A:
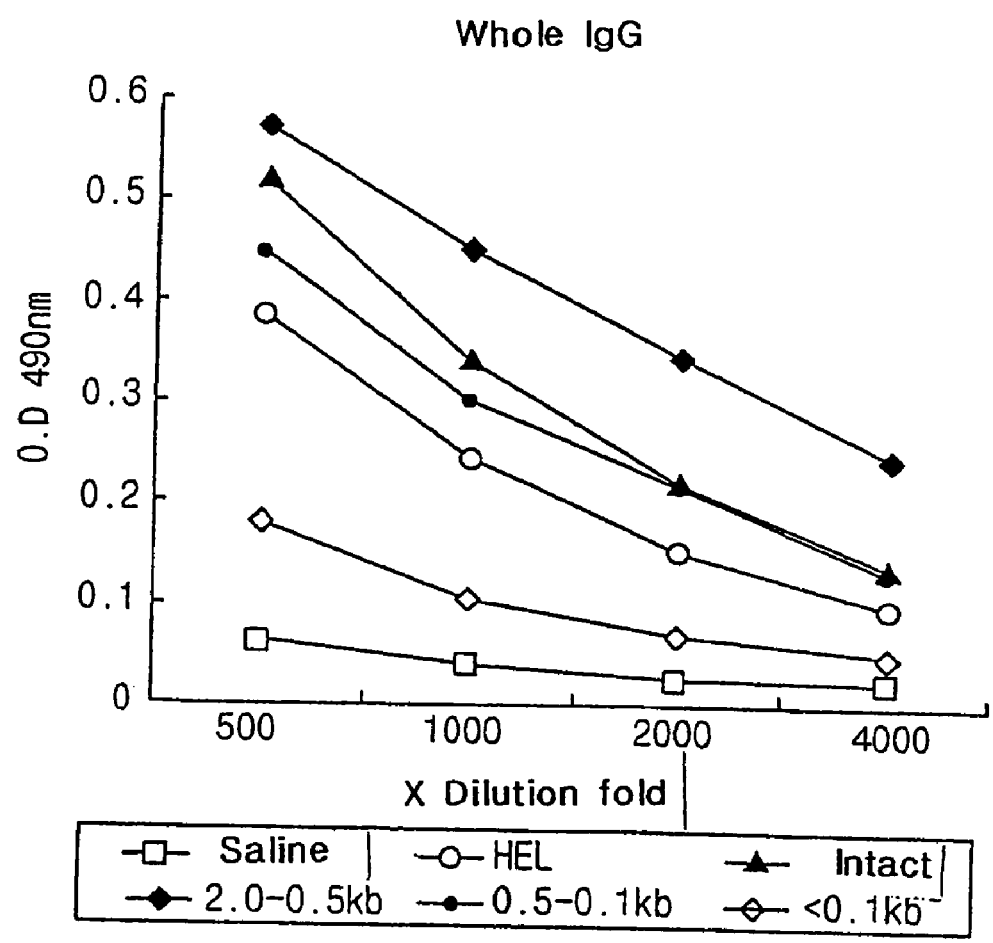
FIGS. 2a to 2c are graphs illustrating the optimal immune increasing effect in *E. coli* DNA (CIA02) of about 2-0.5 kb.

In order to identify immune increase effects of E. coli DNA separated according to size, the effect as immune adjuvant was measured in mouse (see FIG. 2). 50 ug of HEL (Sigma) as antigen and 50 ug of each E. coli DNA as adjuvant were injected (i.p) into ICR mouse (a 4-week old male, 20 g) twice at interval of a week. 7 days after final injection, the whole blood was collected and serum was separated. The antibody value in serum was measured with HEL as antigen using ELISA method (see FIG. 2a).

As analysis results, the size of 2.0~0.5 kb showed the highest antibody value. Thereafter, from repeated experiments, it was shown that about 1 kb represented the optimal effect.

Figure 2B:
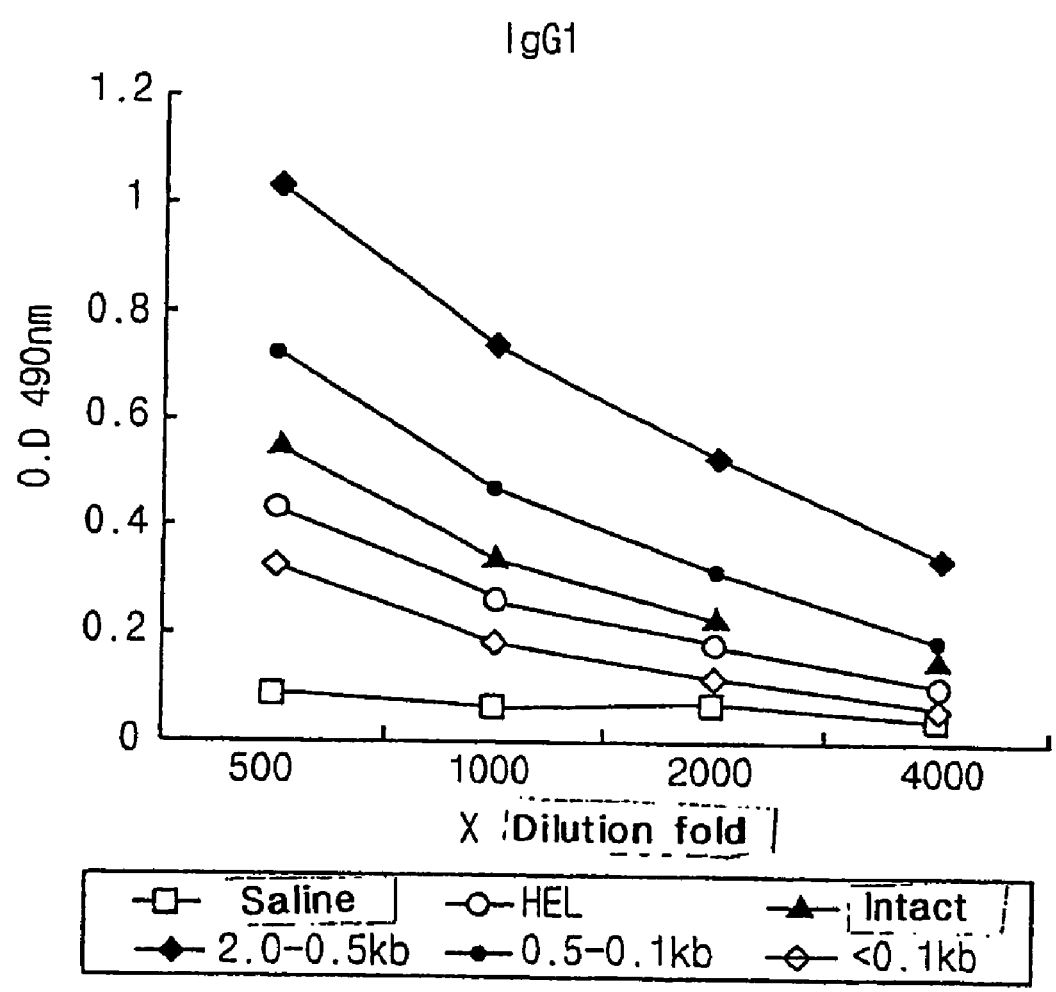
Figure 2C:
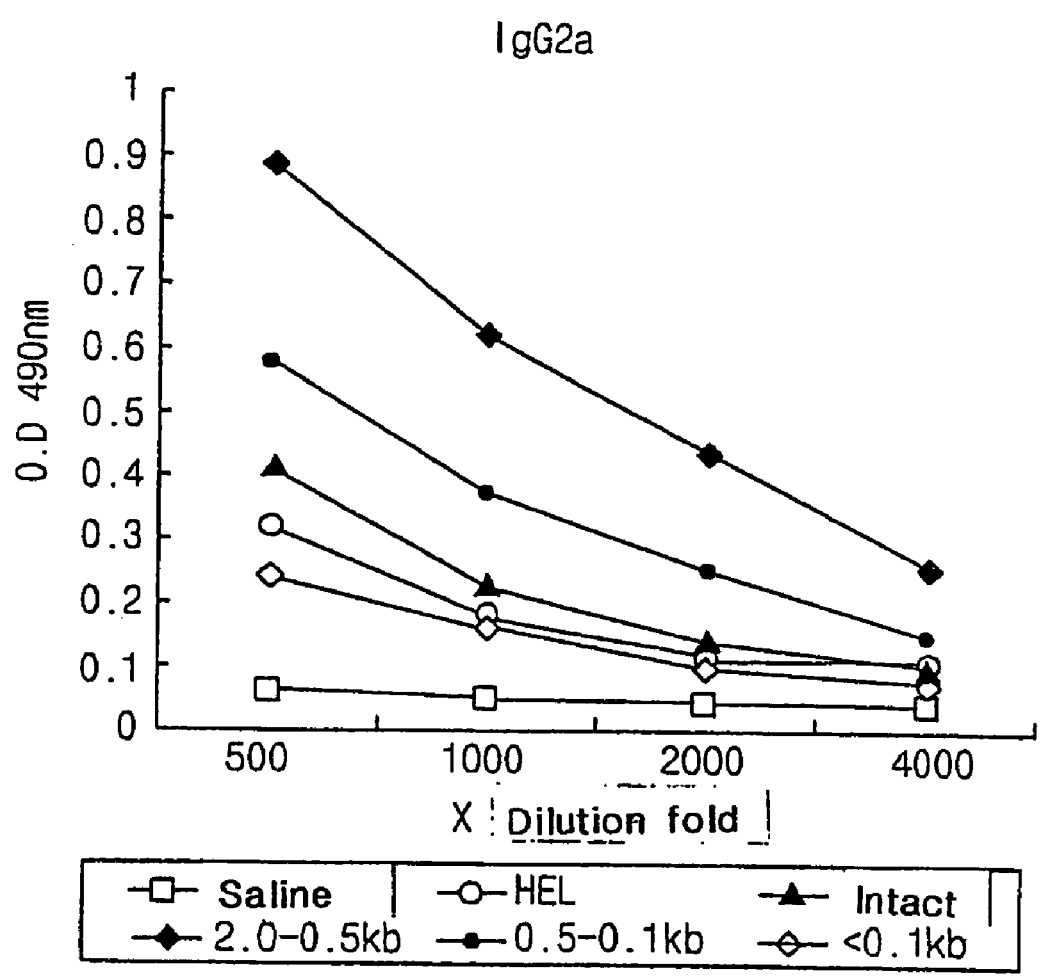

The effects of humoral and cellular immunity in the subclass of antibody in serum was identified with the same ELISA method (see FIGS. 2b and 2c).

The sonication condition for obtaining 1 kb E. coli DNA determined according to the above result is at 7 minutes in 20,000 J.

EXAMPLE 3

Removal of Endotoxin from E. Coli DNA and Measurement of DNA Purity

Removal of Endotoxin

After sonication, DNA was reacted with chloroform at 4° C. for 12 hours, and three volumes of ethanol was treated therein to obtain a precipitate.

The precipitate was treated with Triton X-114 (Sigma) to 0.5% of final concentration. The resulting precipitate was reacted at 4° C. for 4 hours, warmed at 37° C. for 5 minutes and then mixed with penol/chloroform/isoamyl alcohol (25:24:1) at a ratio of 1:1 to obtain water layer.

The obtained E. coli DNA was precipitated with ethanol and dissolves in pyrogen free water.

Endotoxin removed DNA was analyzed with Limulus Amebocyte Lysate (LAL) kit (BioWhittaker QCL-1000) to detect the remaining endotoxin.

Table 1 shows the endotoxin value and yield of purified E. coli DNA (CIA02) after removal of endotoxin according to the above method.

TABLE 2

The endotoxin value and yield of purified E. coli DNA(CIA02)

| Sample Number | DNA Concentration | Amount of the whole DNA (/15 ml) | Pyrogen free DNA | Ratio | Endotoxin (per DNA 1 mg/ml) | Yield |
|---|---|---|---|---|---|---|
| 1 | 3 mg/ml | 45 mg | 16.2 mg | 1.77 | <1 ng | 36% |
| 2 | | | 20.25 mg | 1.66 | <1 ng | 45% |
| 3 | | | 18.9 mg | 1.71 | <1 ng | 42% |

The amount of remaining organic solvent was measured with GC/MSD (gas chromatography/mass selected detector), HP-5890A/HP-5870B. Ethanol, acetone, chloroform and penol were measured with SIM (Selected Ion Monitoring) having the column of 50 m.ultra1 (see Table 2).

TABLE 3

| Remaining organic solvent | Amount of remaining organic solvent | | | |
|---|---|---|---|---|
| | Acetone | Ethanol | Phenol | Chloroform |
| ng/ul | — | 0.813 | — | — |

More than 99% degree of purity was identified by measuring protein contamination per E. coli DNA mg with Brad-Ford method.

EXAMPLE 4

Purification of Lipopolysaccharide (CIA04) from Mutant E. Coli

Purification of Lipopolysaccharide from Mutant E. Coli

E. coli was prepared with the same method as above described DNA isolation method.

The prepared E. coli was mixed with 2 volumes of ethanol thereof, and centrifuged at 4,000 g to obtain a precipitate. 1.5 volumes of acetone of the precipitate was added, mixed and then centrifuged at 4,000 g.

The same amount of ethyl ether was added and mixed in the resulting precipitate, and then centrifuged at 4,000 g. The cell pellet obtained therefrom was covered with aluminum foil and punctured the foil and dried to measure cell mass. Thereafter, 7.5 ml of extraction mixture (90% penol: chloroform: petroleum ether=2:5:8) was added per 1 g of cellular dry weight.

The resulting solution was divided into glass centrifuge tube and centrifuged at 25° C.; 3,000 rpm (1,200 g) for 20 minutes to obtain supernatant. The supernatant was left in hood for 12 hours. Then, the solution was divided into glass centrifuge tube and lipopolysaccharides dissolves in ethyl ether by centrifugation at 25° C., 3,000 rpm (1,200 g) for 20 minutes, and then transferred into eppendorf tube. The solution was dried in hood, and dried weight was measured with chemical balance. Then, ethanol was added therein and stored before use.

Figure 3:
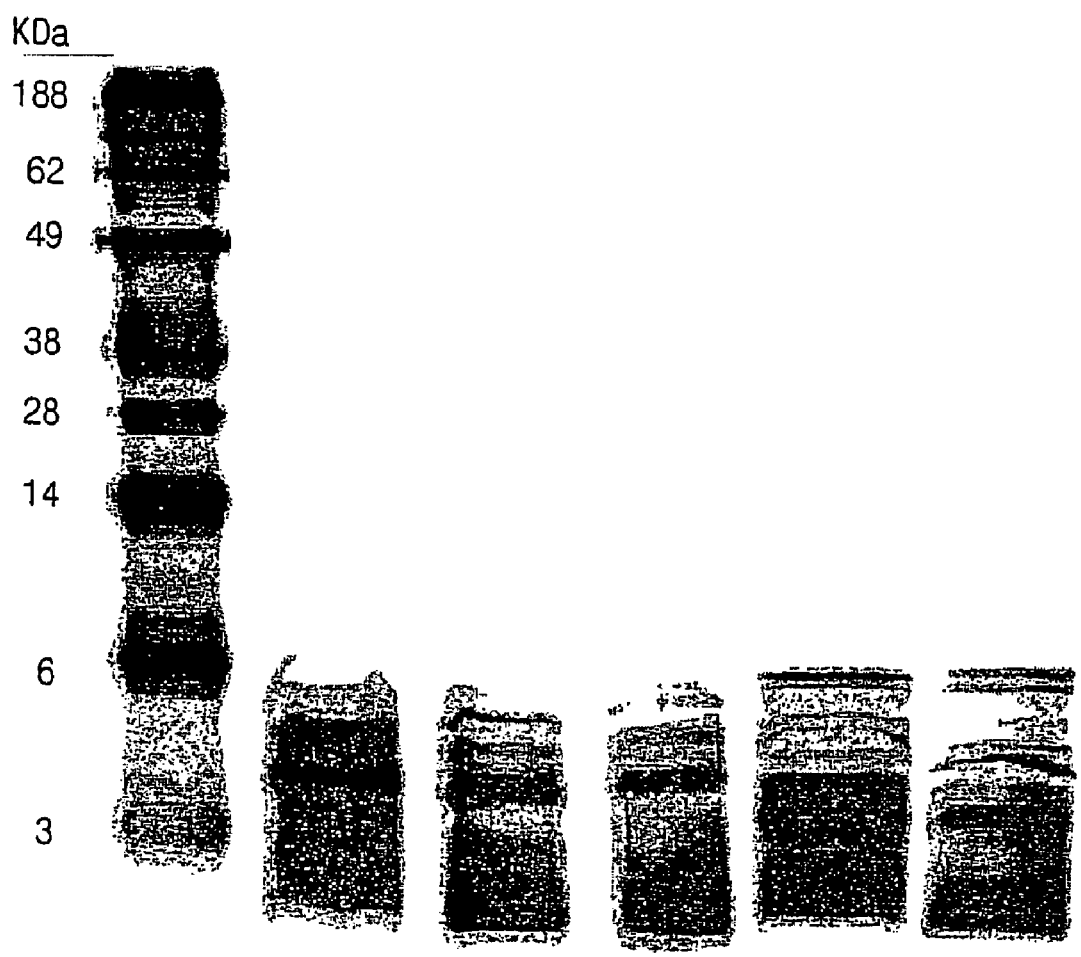
FIG. 3 is a picture illustrating lipopolysaccharide product isolated from *E. coli* outermembrane. The picture illustrates isolated lipopolysaccharide according to 5 times batch.

After ethanol was completely eliminated in purified E. coli lipopolysaccahride stored in ethanol, the amount of KDO (2-Keto-3-deoxyoctonate) in lipopolysaccharide was measured with lipopolysaccharide standard (Lsit Biological Lab.). After the concentration was measured from the standard, the lipopolysaccharides were analyzed with SDS-PAGE according to size and identified by silver staining (see FIG. 3). The lipopolysaccharide had molecular weight ranging from about 5,000 to 10,000, and its size was very small compared with general E. coli lipopolysaccharide.

EXAMPLE 5

Removal of Toxicity in Purified Lipopolysaccharide from Mutant E. Coli

Removal of Toxicity in Lipopolysaccharide by Lipid A Degradation

Purified E. coli lipopolysaccharides diluted to 3 mg/ml of concentration and mixed with 0.2N NaOH at a ratio of 1:1. The resulting solution was shaken every 10 minutes at 60° C. and deacylated for 140 minutes.

About 1/5 volumes of initial 0.2N NaOH of 1N acetic acid was added in the resulting solution to titrate pH 7.0.

After pH titration, ethanol-precipitated non-toxic lipopolysaccharide was obtained.

After the concentration of non-toxic lipopolysaccharide was measured with KDO method, its size change was identified by SDS-PAGE and silver staining in comparison with lipopolysaccharide before treatment.

Figure 4:
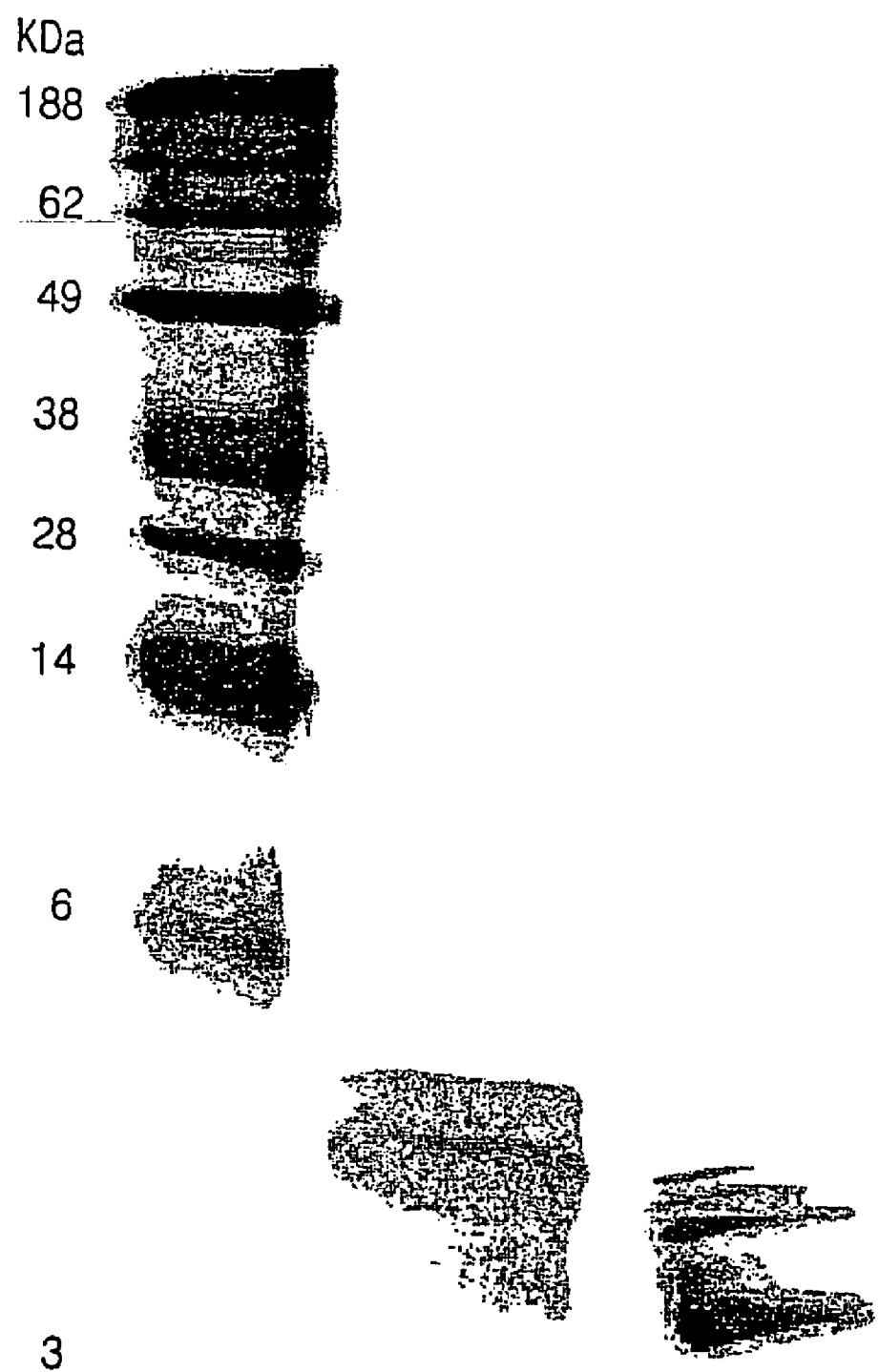
FIG. 4 is a picture illustrating that the size of isolated *E. coli* lipopolysaccharide treated with alkali is changed by degrading lipid A and lose toxicity by this treatment, wherein Lane 1 represents isolated lipopolysaccharide product CIA04 and Lane 2 alkali-treated non-toxic lipopolysaccharide CIA05.

As a result of staining, it was shown that lipid A of lipopolysaccharide was degraded by alkali treatment and the size of lipopolysaccharide became smaller (see FIG. 4).

Confirmation of Toxicity Removal of Non-Toxic Lipopolysaccharide

In order to test stability of non-toxic lipopolysaccharide, experiments on secretion, pyrogenicity and abnormal toxicity of inflammatory proteins were performed.

Experiment on Secretion of Inflammatory Protein

THP-1 (Acute monocytic leukemia) was treated with non-toxic lipopolysaccharide from high to low concentration to measure the amount of secreted TNF-α in comparison with the control group of purified lipopolysaccharide.

Figure 5:
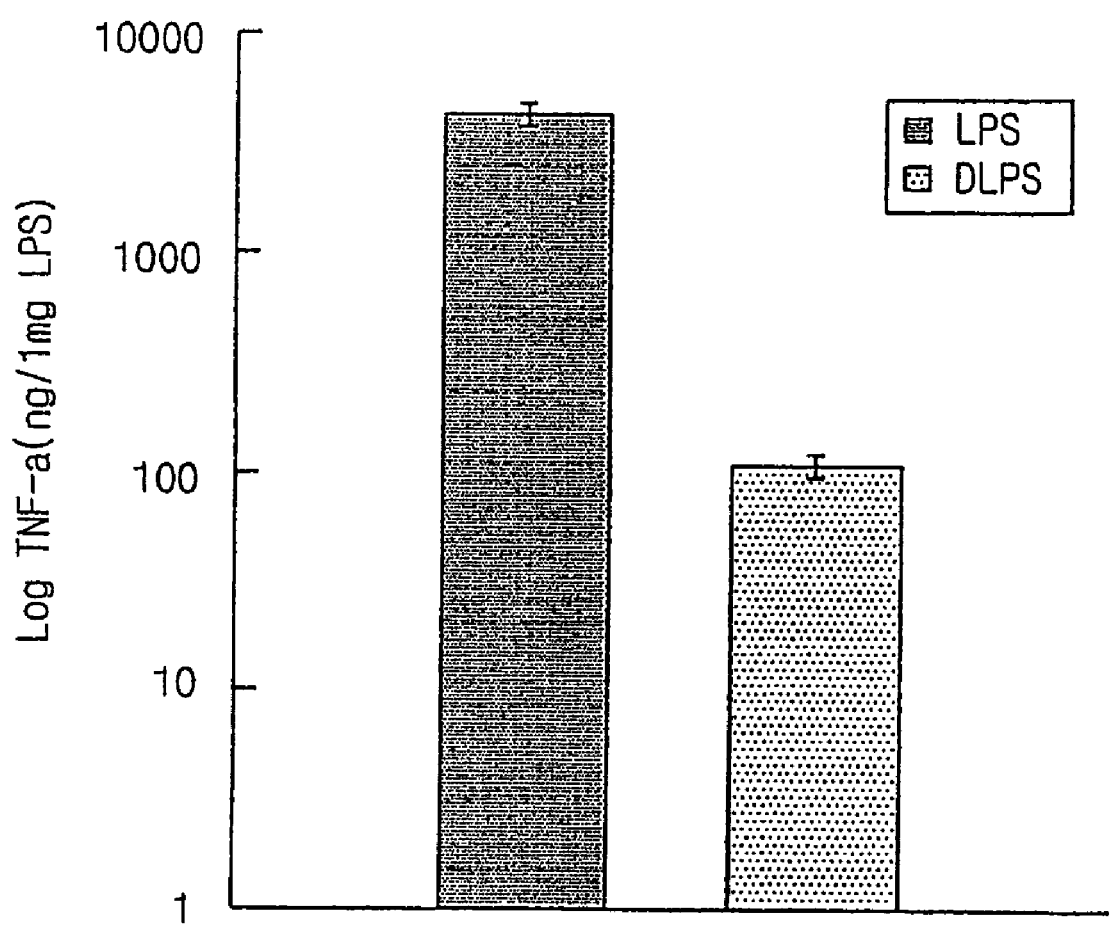
FIG. 5 is a graph illustrating the decrease of TNF-α secretion in THP-1 cell line treated with the non-toxic lipopolysaccharide (CIA05).

While 5 pg TNF-α was secreted in 1 ug of lipopolysaccharide in the control group, 0.1 pg TNF-α was secreted in 1 ug of non-toxic lipopolysaccharide. Here, it was shown that inflammatory reaction induced by toxicity decreased by 50 times. Additionally, it was shown that the amount of TNF-α secreted in *E. coli* DNA was below 100 fg. As a result, the non-toxic lipopolysaccharide was proved to be very safe material (see FIG. 5).

Experiment on General Safety Test

The sample of high dose was injected in more than two kinds of rodents to observe abnormal weight change.

and its needle were heat-sterilized at 250° C. for over 30 minutes. Only water was fed from 16 hours before use to completion of the experiment. The animals were fixed not as tight as possible.

The body temperature was measured by inserting the thermometer into the rectum to a constant depth ranging from 60 to 90 mm for constant time. The temperature measured before injection was defined as a control temperature. The sample heated at 37° C. was injected into the ear vein within about 15 minutes after the control was measured. The body temperature was measured every 3 hours, at least 1 hour, after injection. Gap between the control temperature and sample temperature was defined as difference in temperature. The maximum value of the difference in temperature was defined as pyrogen reaction of the experimental animals. Here, the samples of three animals were used.

Pyrogenic material experiment was negative when the total of three animals was below 1.3° C. while positive when over 2.5° C. These experiments were performed three times, and the negative reaction was suitable for these pyrogenic material experiments.

The results are shown in Table 4.

TABLE 4

| The No. of time | Number | Before injection (three times measured) | | | After injection (hrs) | | | | | | increased bod Temp. | Sum of increase body Temp. | Result | standard |
|---|---|---|---|---|---|---|---|---|---|---|---|---|---|---|
| | | 1 | 2 | 3 | 0.5 | 1 | 1.5 | 2 | 2.5 | 3 | | | | |
| 1 | 1 | 39.1 | 39.2 | 39.2 | 39.4 | 39.3 | 39.2 | 39.2 | 39.1 | 39.1 | 0.2 | 0.8 | pass | <1.3° C. |
| | 2 | 39 | 39.1 | 39.3 | 39 | 39.2 | 39.5 | 39.2 | 39.1 | 39.3 | 0.4 | | | |
| | 3 | 39.4 | 39.2 | 39.2 | 39.3 | 39.5 | 39.3 | 39.5 | 39.3 | 39.4 | 0.2 | | | |
| 2 | 1 | 39 | 39.3 | 39.1 | 39.4 | 39.2 | 39.3 | 39.1 | 39.2 | 39 | 0.4 | 1.7 | pass | <3.0° C. |
| | 2 | 39.4 | 39.2 | 39.2 | 39.1 | | 39.3 | 39.1 | 39.2 | 39.2 | 0.3 | | | |
| | 3 | 39.3 | 39.3 | 39.2 | 39.4 | 39.4 | 39.4 | 39.4 | 39.3 | | 0.2 | | | |
| 3 | 1 | 39.2 | 39.2 | 39.1 | 39.2 | 39.2 | 39 | 39.2 | 39.1 | 39.1 | 0.2 | 2.5 | pass | <5.0° C. |
| | 2 | 39.1 | 39.5 | 39 | 39 | 39.1 | 39.2 | 39.1 | 39.3 | 39.2 | 0.4 | | | |
| | 3 | 39.2 | 39.3 | 39.2 | 39.3 | 39.2 | 39.3 | 39.2 | 39.4 | 39.3 | 0.2 | | | |

A. Experiment in Guinea Pig

About 350 g of a guinea pig showed no abnormality and gained weight gradually when observed for more than 5 days before use.

The 5 ml of sample was used per one guinea pig.

The sample was one time injected (i.p) into more than two guinea pigs, and they were observed for more than 5 days.

B. Experiment in Mouse

An about 5-week old mouse showed no abnormality and gained weight gradually when observed for more than 5 days before use.

The sample was one time injected (i.p) into more than two mice, and they were observed for more than 7 days.

The sample was proved suitable in this experiment when an animal showed no abnormality during the observation period.

Figure 6A:
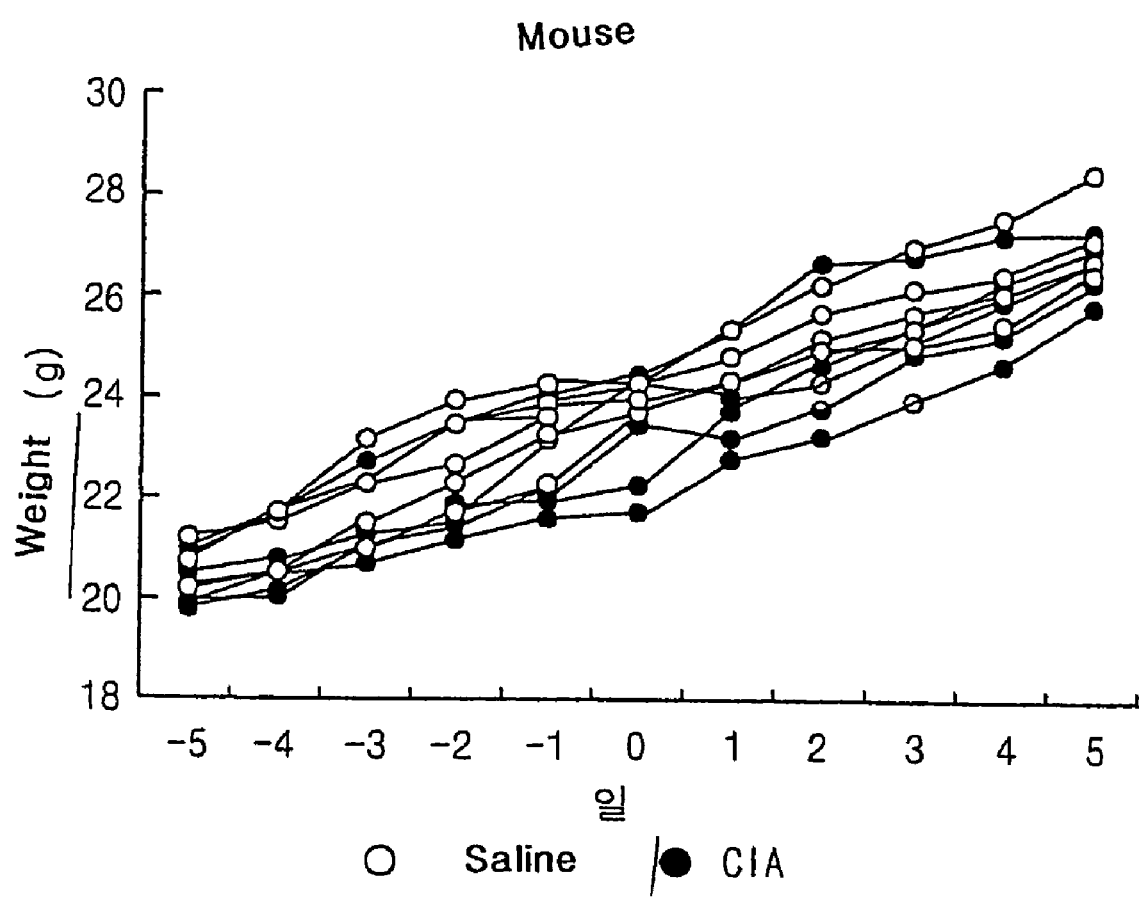
FIG. 6a is a graph illustrating results of general safety test on the non-toxic lipopolysaccharide (CIA05) in mouse.
Figure 6B:
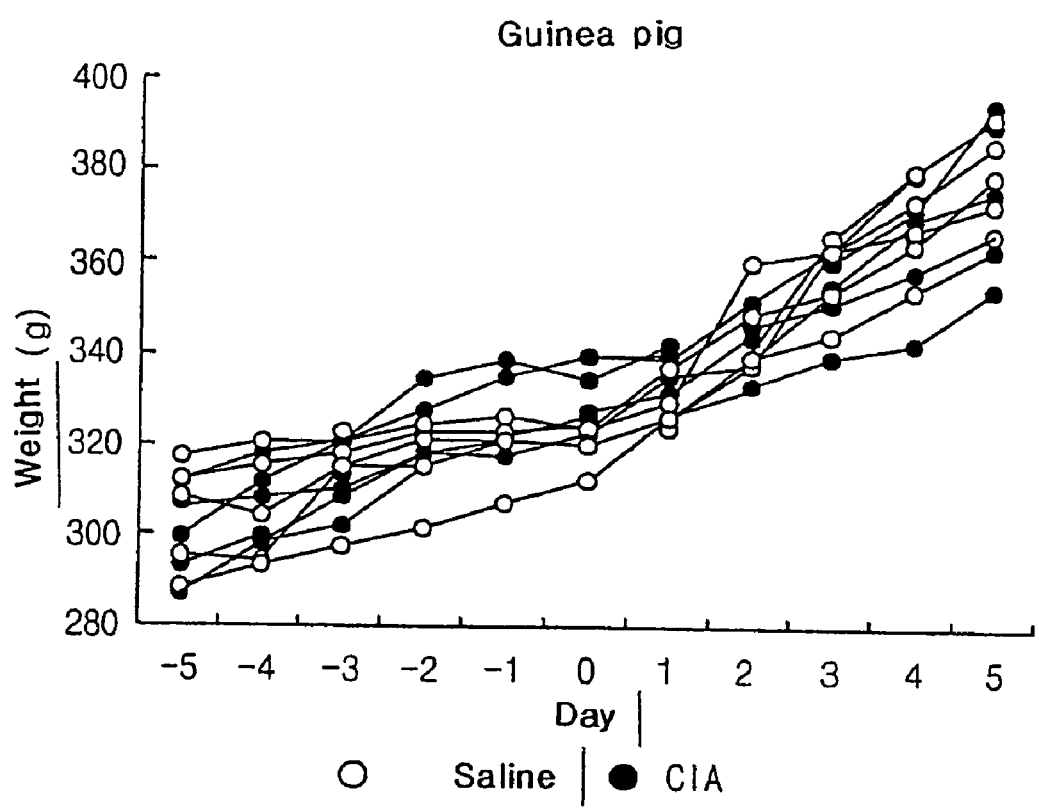
FIG. 6b is a graph illustrating results of general safety test on the non-toxic lipopolysaccharide (CIA05) in guinea pig.

As an experimental result, no abnormal weight change was observed after injection of the sample (see FIG. 6a).

Pyrogenicity Experiment

After vaccine was injected into three rabbits, change in the rectal temperature was observed. The 0.2 ug/ml of sample per 1 kg of rabbit was injected in ear vein of rabbit. Then, the change in abnormal temperature was measured by inserting a thermometer into the rectum.

Here, the weight of rabbits was over 1.5 kg. The rabbits were reused more than 3 days after they had been used in experiments. The body temperature was measured with an apparatus measuring the temperature up to 0.1° C. An injector

EXAMPLE 6

Combine *E. Coli* DNA Fragment (CIA02) and Non-Toxic Lipopolysaccharide (CIA05) and Identification of Activity Combine *E. coli* DNA Fragment (CIA02) and Non-Toxic Lipopolysaccharide (CIA05)

The *E. coli* DNA (CIA02) and non-toxic lipopolysaccharide (CIA05) prepared according to each standard method was mixed to determine the optimal mixing method and dose.

In order to identify the change in effect according to mixing method, the antigen was treated with two different chemical materials (MPBH and SPB) for binding. CIA02 and CIA05 were combined with the modified antigen. In another way, CIA02, CIA05 and the antigen were mixed and shaken. Additionally, immune increase effects in each dose were analyzed. In order to identify the effect of immune adjuvant in mouse, 0.1 ml of 50 ug HEL (Sigma) as antigen was injected (i.P) into ICR mouse (a 4-week old male, 20 g) two times at the interval of a week. 7 days after final injection, the whole blood was collected and serum was separated therefrom. The antibody value in serum was analyzed using HEL as antigen by ELISA method (see FIG. 7a).

The control group was 0.5 and 1 ug of LPS(CIA04) while the experimental group was antigen, 0.5 ug of CIA05 and 50 ug of CIA, shaking mixing group consisting of antigen, 1 ug of CIA05 and 50 ug of CIA, modified antigen, 0.5 ug of CIA05 and 50 ug of CIA, combining group consisting of modified antigen, 1 ug of CIA05 and 50 ug of CIA respectively.

Figure 7A:
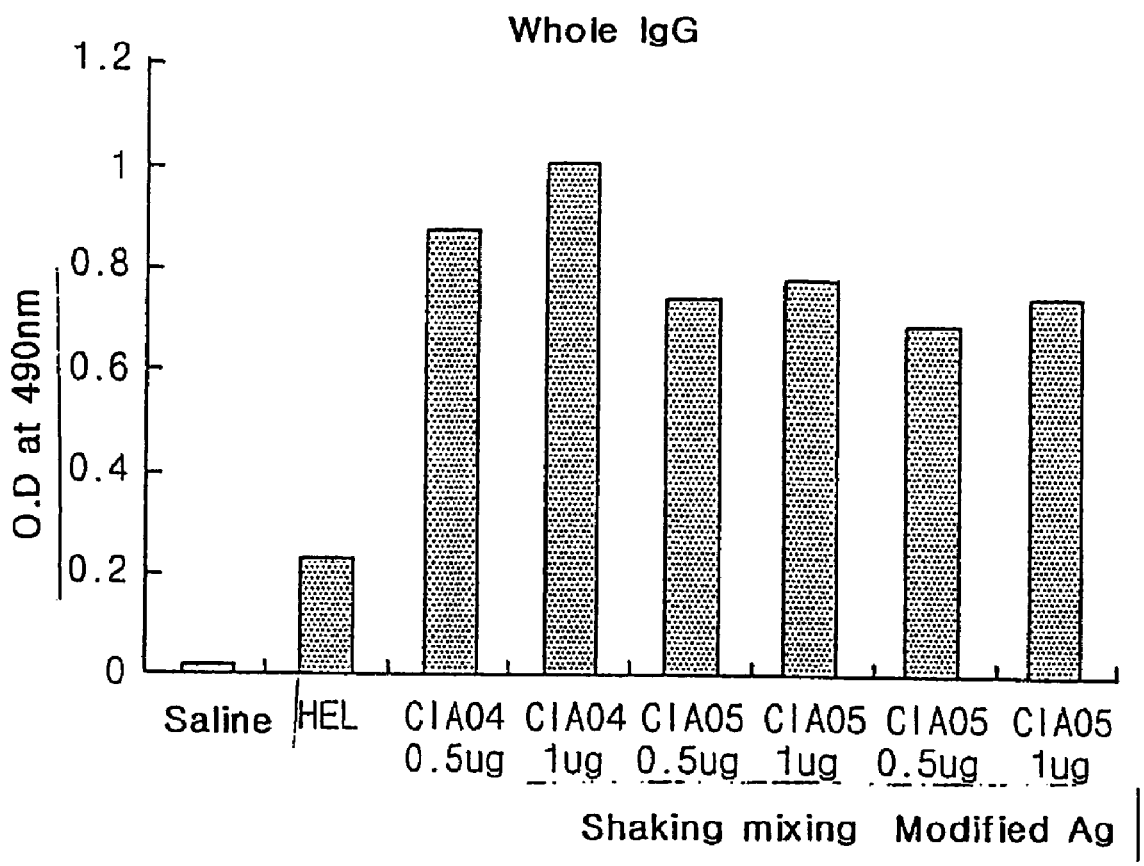
FIGS. 7a to 7c are graphs illustrating immune increase effect according to combination method and concentration of *E. coli* DNA (CIA02) and non-toxic lipopolysaccharide (CIA05).
Figure 7B:
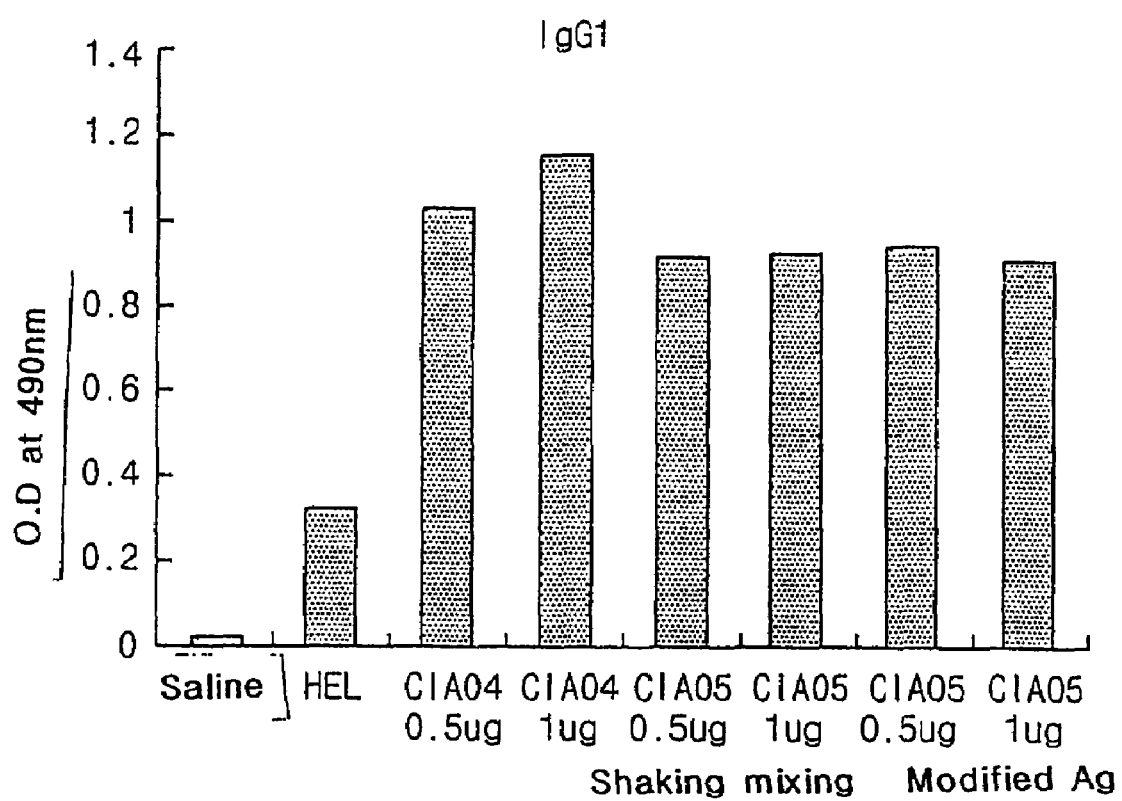
Figure 7C:
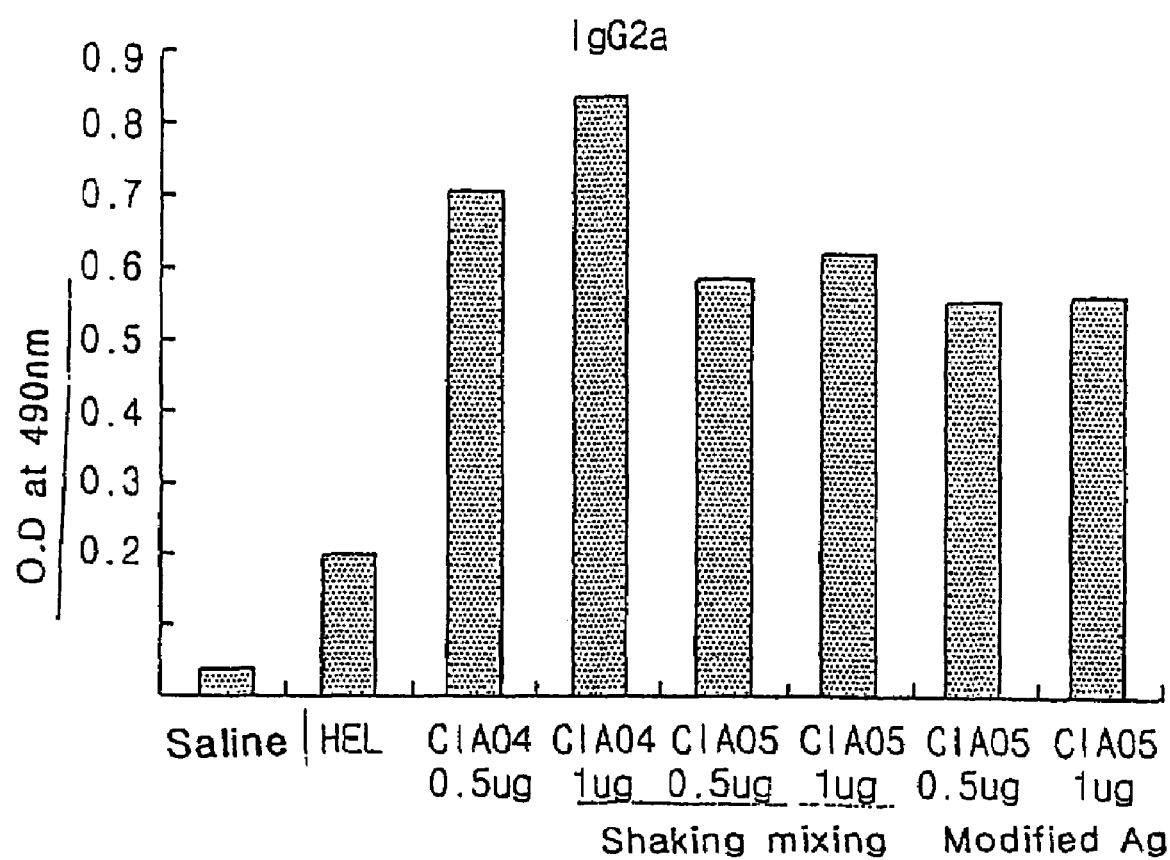

As an experimental result, it was proved that LPS(CIA04) represented the highest antibody activity but it was not suitable for anti-cancer adjuvant because of side effects of toxicity (see FIG. 7a). Although combining methods made little difference, a shaking mixing method was more superior to the other methods. Particularly, it was shown that the shaking mixing method was effective because it showed a difference in IgG2a related to cellular immunity among immunoglobulin subclass (see FIG. 7b). In yield, the shaking mixing method was simple and had no loss during treating processes. As a result, the shaking mixing method was selected. The dose was determined according to the amount of CIA05. The dose of 1 ug showed more superior efficacy than that of 0.5 ug. As a result, the dose of 1 ug was determined.

The effects of humoral and cellular immunity in subclass of antibody in serum were analyzed with ELISA method.

Experiment Compared with the Conventional Immune Adjuvant

Figure 8A:
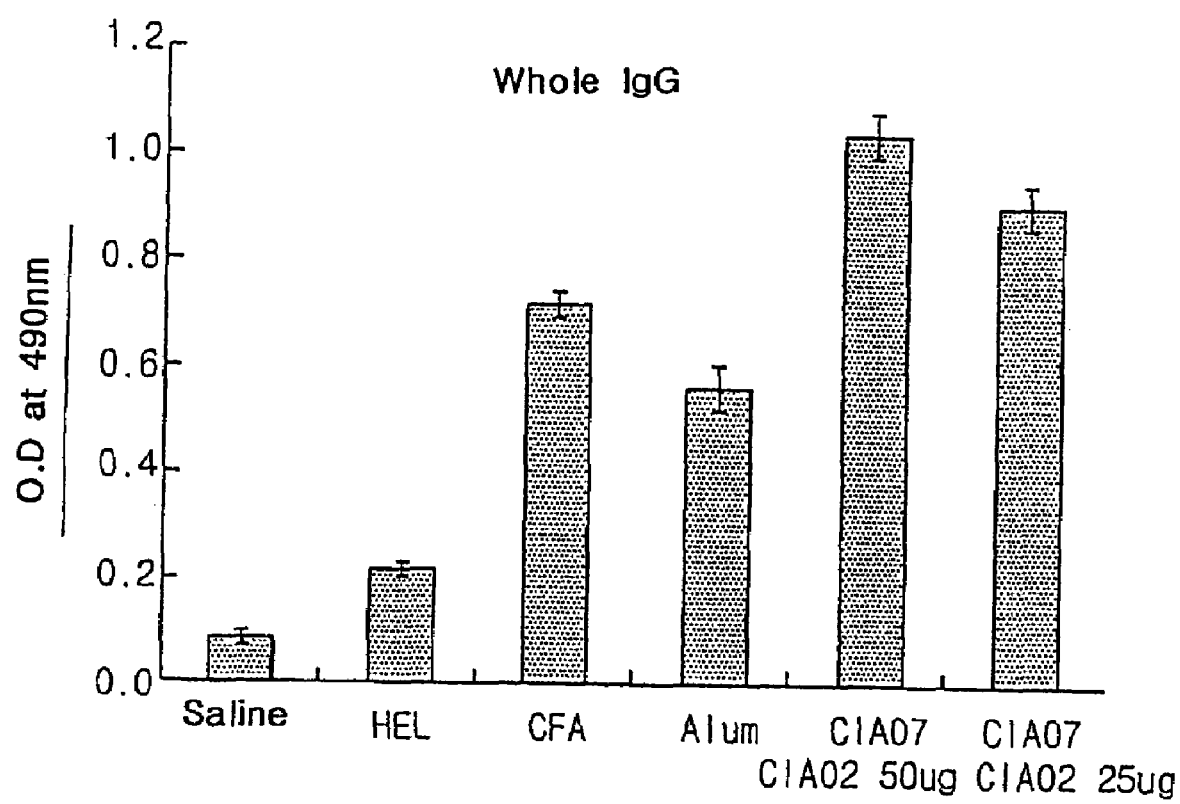
FIGS. 8a to 8c are graphs illustrating immune increase effects of *E. coli* derived CIA07 in comparison with other immune adjuvants.

In order to test immune increase effects of the determined making method and dose, an experiment was performed in comparison with those of the conventional immune adjuvant (see FIG. 8a).

Applicability for CIA07 as immune adjuvant was analyzed through animal experiments. 0.1 ml of 50 ug HEL (Sigma L-6876) as antigen was injected (i.P) into ICR mouse (a 4-week male, 20 g) twice at the intervals of a week. 7 days after final injection, the whole blood was collected and serum was separated therefrom. The antibody activity in serum was analyzed with HEL as antigen using ELISA method.

Figure 8B:
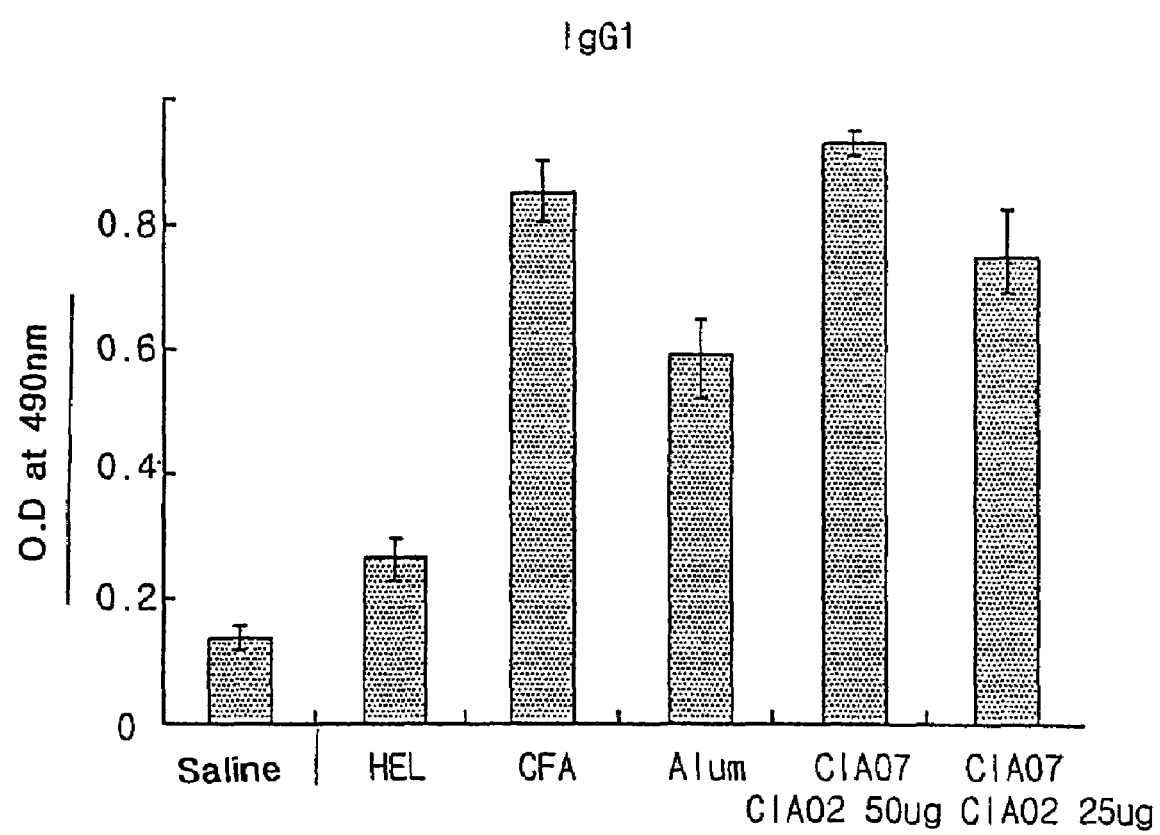
Figure 8C:
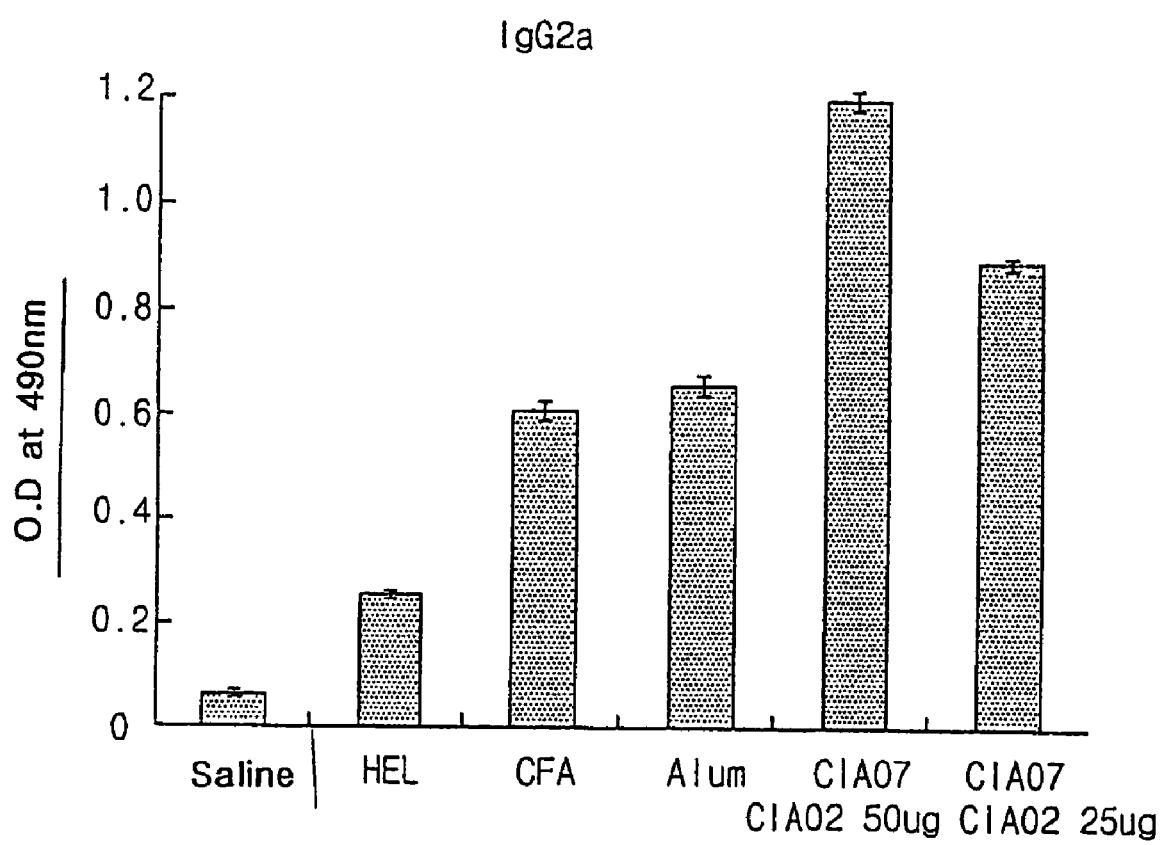

It was shown that the antibody activity of CIA07 represented the same effect of CFA (complete Freund's adjuvant), the conventional immune adjuvant for animal experiment, and Alum (aluminium hydroxide gel) only authorized in use for human (see FIG. 8a). However, as a result of analyzing isotype switching, it was shown that the conventional immune adjuvants such as CFA and Alum activated immunization of Th(T helper)-2 type wherein antibodies of IgG1 were mainly produced while CIA07 induced immune activation of Th(T helper)-1 type wherein antibodies of IgG2a rather than IgG1 were specifically produced (see FIGS. 8b and 8c).

In order to identify the dose of CIA02, 1 ug of CIA05 was mixed in 25 ug and 50 ug of CIA02, respectively. As an analysis result, it was shown that the antibody activity was changed according to the dose. Accordingly, 50 ug of CIA02 and 1 ug of CIA05 were determined for the optimal dose.

Identification Experiment CIA Activity with Whole Blood Analysis

Figure 9:
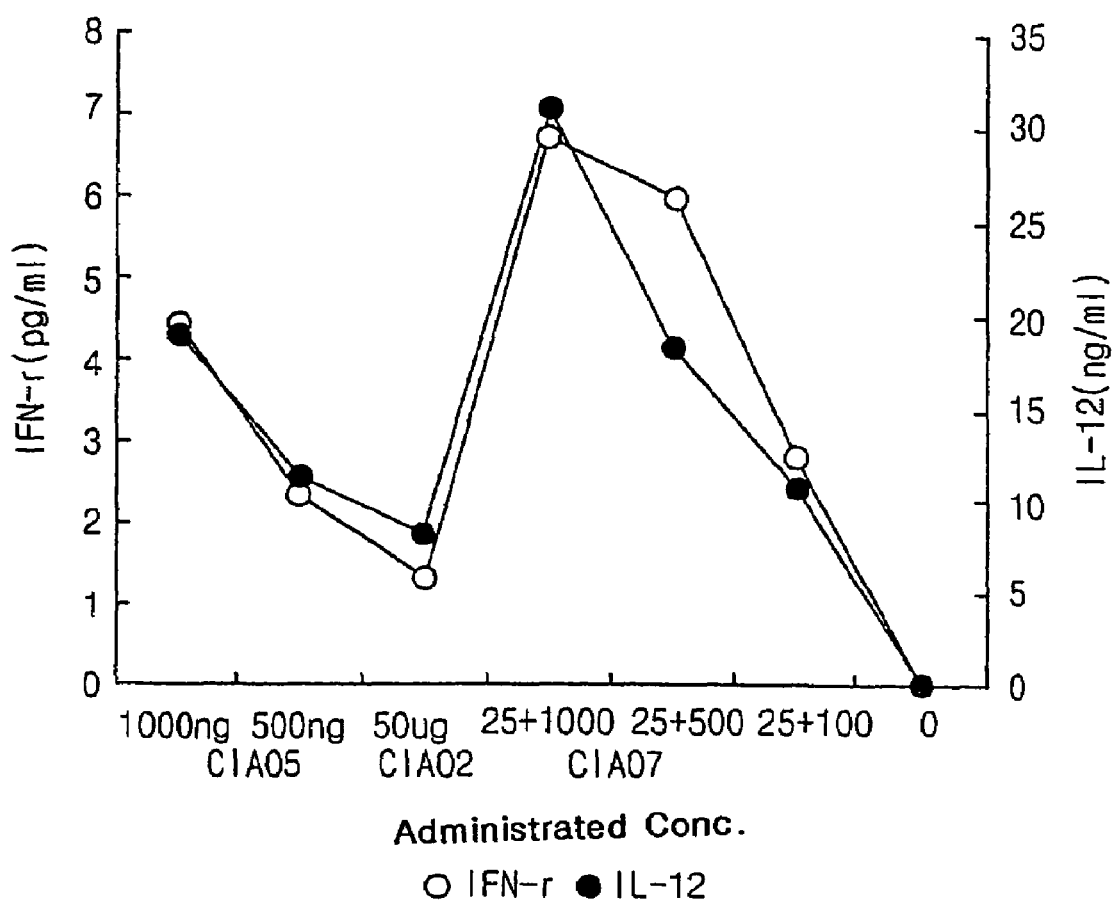
FIG. 9 is a graph illustrating cytokine secretion in human whole blood treated with *E. coli* derived anti-cancer treatment CIA07.
Figure 10A:
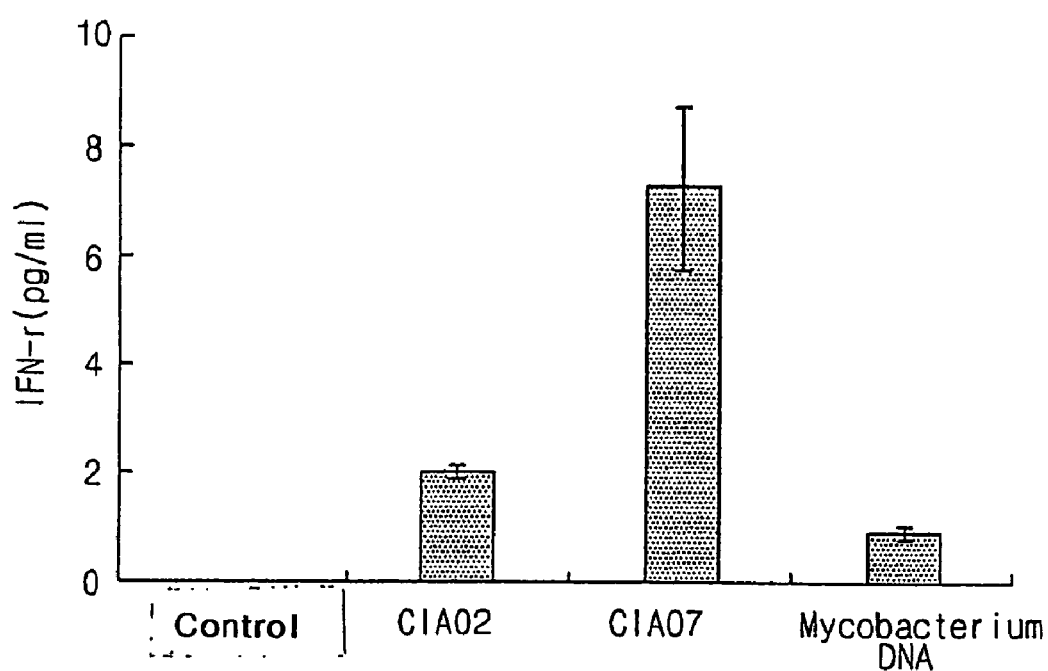
FIGS. 10a to 10b are graphs illustrating the amount of cytokine secretion in human whole blood treated with *E. coli* derived anti-cancer treatment CIA07 and mycobacterium DNA.
Figure 10B:
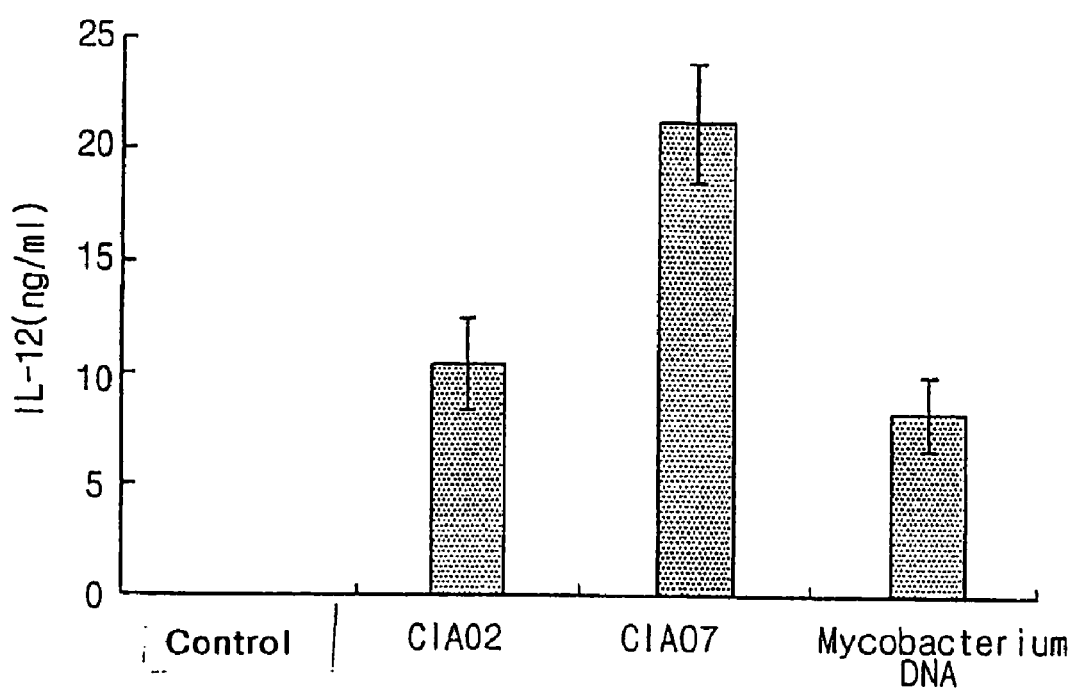

Venous blood from healthy male adult was sterilely obtained in vacuum tube having heparin as anticoagulant. The whole blood obtained therefrom was mixed with RPMI 1640 culture medium (2 mM L-glutamine, 1 mM Sodium pyruvate, gentamycin of 80 ug/ml) at a ratio of 1:1. 20 ul of CIA07 50 ug of CIA02+1 ug or 500 ng, 100 ng of CIA05) or 20 ul of HBSS were added in 1 ml of the whole blood mixed with culture medium and then incubated in 5% $CO_2$ culture medium at 37° C. for 24 hours. The secretion amount of IFN-γ (R&D system, 210-TA-010) and IL-12 p40(R&D system, 2219-IL-005) was analyzed in supernatant liquid in the culture medium with ELISA kit. The results were shown in FIG. 9.

In the same way, 20 ul of CIA07 (50 ug of CIA02+1 ug of CIA05), CIA02 (50 ug), *Mycobacterium* DNA (50 ug) or HBSS (20 ul) were added in 1 ml of the whole blood mixed with culture medium. Then, cytokine secretion was analyzed.

As an analysis result, the synergic immune increase effect was represented in case of addition of mixed CIA02 and CIA05 more than in case of addition of only CIA02 or only CIA05. The best result was shown in the dose of 50 ug of CIA02 and 1 ug of CIA05. In comparison with mycobacterium DNA, CIA07 represented the excellent result as well as CIA02.

Luciferase Assay

Raw cells were spread in 12 well plates by $5 \times 10^4$ cells (1 ml DMEM/10% FBS) per a well, and cultured in $CO_2$ incubator at 37° C. for 24 hours. IL-12 luciferase reporter plasmid (0.2 ug/well) mixed with PRL-null plasmid (20 ng/well) was added in serum free DMEM (50 ul/well) mixed with Fugene 6 (1.5 ul/well, Roche Cat. No. 1 814 443), transfection reagent, and then left for 5 to 10 minutes. The resulting mixture was added in the Raw cells by 52 ul/well, and incubated in $CO_2$ incubator at 37° C. for 24 hours. Thereafter, Raw cells were treated with CIA07 (CIA02 20 ug+ CIA05 400 ng per a well) and incubated in $CO_2$ incubator at 37° C. for 12 hours. Luciferase reaction carried out by luciferase assay kit (Promega Cat. no. E1500) to measure luciferase activity with luminometer.

Figure 11A:
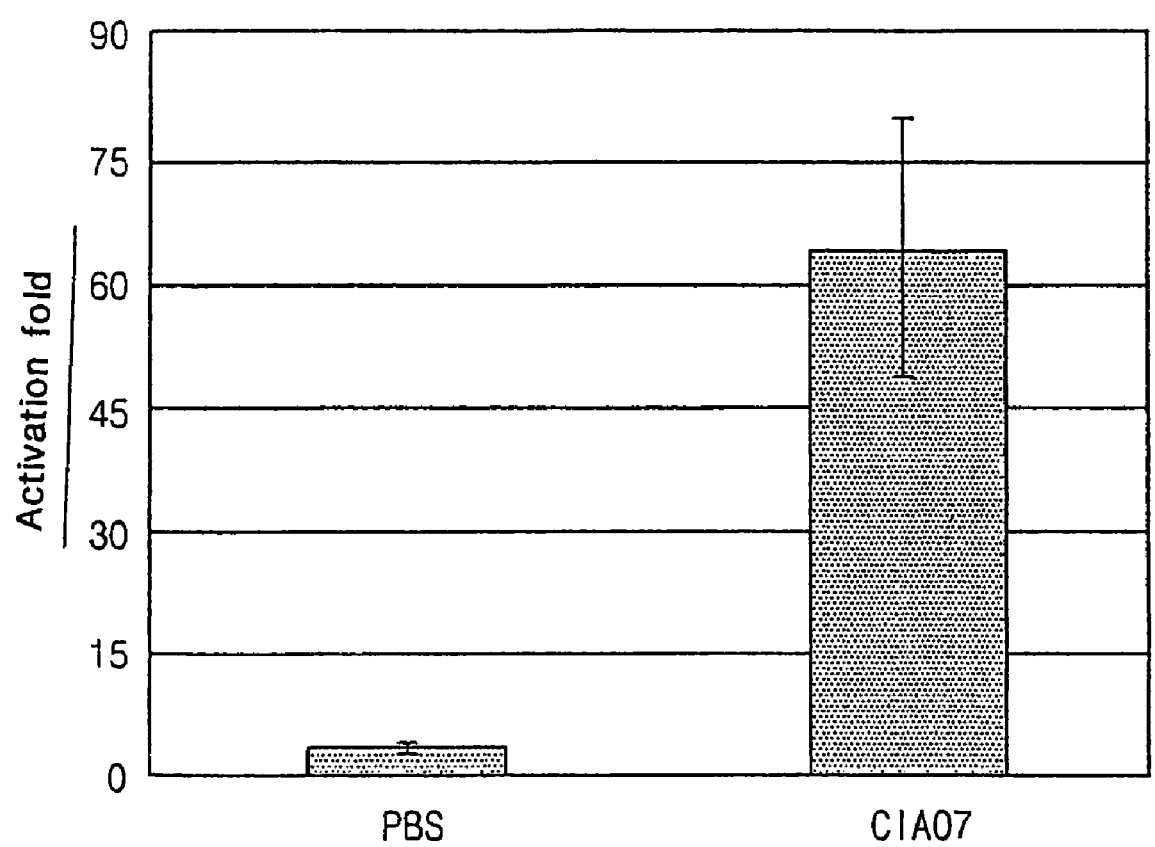
FIGS. 11a to 11b are graphs illustrating the increase of promoter activity by NF-kB activation after treating *E. coli* derived anti-cancer treatment CIA07 in raw cells.
Figure 11B:
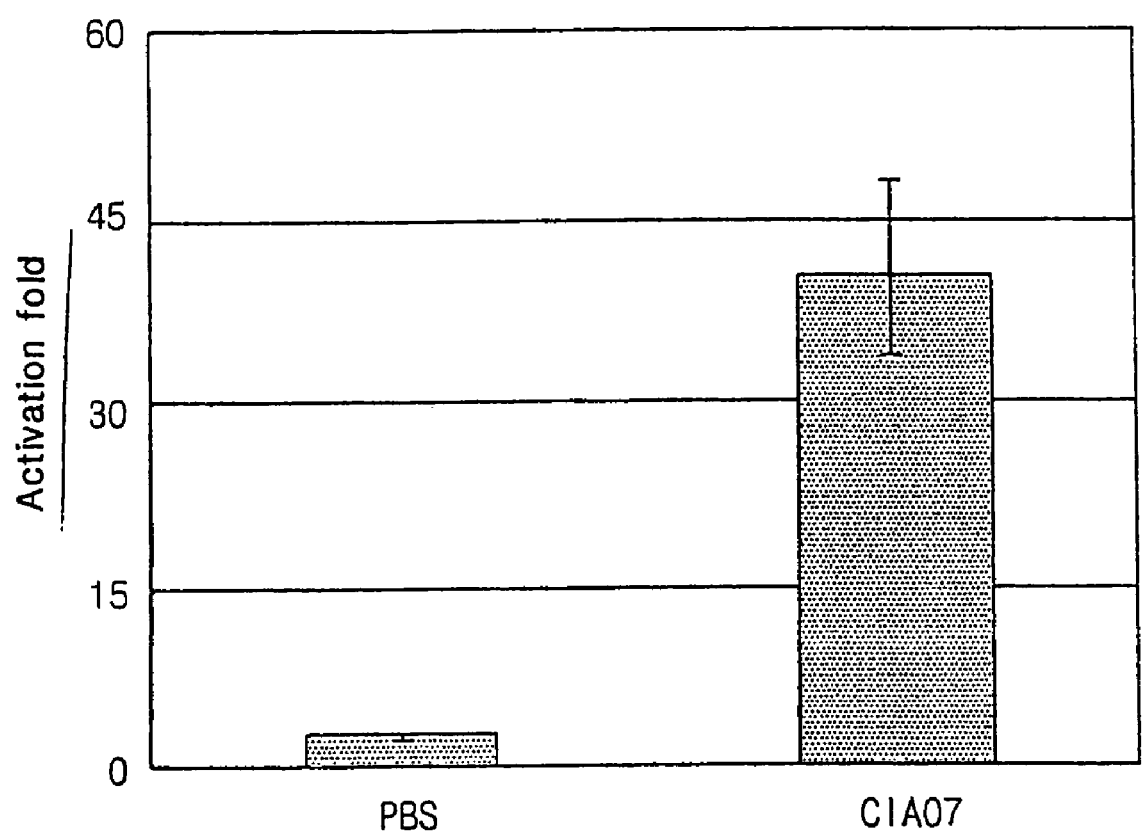

As a result of measuring luciferase activity to identify effects of CIA07 on IL-8 and IL-12 promoter activity, NF-kB binding site existed in IL-8 and IL-12 promoters in common. It was shown that NF-kB was activated in RAW264.7 cell line by CIA07 to increase activity of promoters (see FIG. 11).

Measurement of Anti-cancer Treatment Effect Using Cell Lysis Activity of CIA

Cancer cell killing activity by CIA07 was measured using $_{51}$Cr-release.

Antigen only or with CIA07 was injected under the skin of the bottom of the foot of a 5~8 week old male C3H/HeN mouse.

RPMI-1640 (10 mM HEPES, 100 units/ml penicillin, 100 μg/ml sterptomycin, 300 μg/ml glutamine; Gibco Laboratories, Grand Island, N.Y.) was used for the basal culture medium for culturing cell lines. Inactivated 10% fetal bovine serum (Gibco Laboratories, Grand Island, N.Y.) heated at 56° C. for 30 minutes was added in the basal culture medium. In order to measure activity of LAK cells and cancer cell mediated killing activity, Sarcoma 180 and mouse bladder cancer cell line (MBT-2) were used for target cells.

In order to prepare reaction cell lines, a rat of the experimental group were killed using cervical dislocation. Its spleen was sterilely isolated and minced on stainless steel wire netting using scissors. The fragments were ground and filtered using a glass stick with adding phosphate buffered saline. Then, tissue debris was removed passing through wire netting. After single cell suspension was identified under microscope, cells were washed using the basal culture medium one time. The cells were suspended in 0.84% ammonium chloride solution at 37° C. for 5 minutes to dissolve erythrocyte. The cells were further washed using the basal culture medium two times and suspended in complete culture medium. The cell suspension was divided into culture flasks and cultured in $CO_2$ constant temperature and humidity chamber at 37° C. for 1 hour. Cells that were not attached to the flasks were obtained therefrom, and survival cell number was measured using trypan blue dye exclusion method. Then, $5 \times 10^6$ cells were obtained using the complete culture medium and survival cell number thereof was measured using trypan blue dye exclusion method. Then, $5 \times 10^6$ cell/ml of cell suspension were made using the complete culture medium.

Target cell line was cultured and the number of cells was counted. $10^6$ cells were obtained and the cells were centrifuged at 300 g, 3 minutes. The supernatant liquid except 0.2~0.3 ml was removed using Pasteur pipette without damaging precipitated cells. 100 Ci $Na_{2.51}CrO_4$ (1 ml Ci/ml, NEZ 030S, NEN, USA) was added and labeled in shaking thermostat at 37° C. for 1 hour. The cells were washed using the basal culture and survival cell number thereof was measured using trypan blue dye exclusion method. The labeled target cells were re-suspended in the complete culture medium to $5\times10^4$ cell/ml.

The labeled target cells were divided by 0.1 ml to put $5\times10^3$ cells per a well on 96 well fine plate having a round bottom. 0.1 ml of reactions cell was added at a ratio of reaction cell:target cell=100:1. The cells were cultured in 5% $CO_2$ constant temperature and humidity chamber at 37° C. for 4 hours. After more than 3 wells per an experiment were made and the culture for 4 hours was finished, the cells were centrifuged at 500 g for 15 minutes. Radioactivity was measured in the 0.1 ml of supernatant liquid from each well using gamma counter (Packard, USA). Here, in order to induce the maximum emission, 0.1 ml of 5% triton X-100 (Sigma, USA) was added in the control well group. In order to measure natural emission, the labeled cells were cultured in the complete culture medium having the same dose. The cell toxicity was calculated according to the following formula:

Cytotoxicity(%)=(ER−SR/MR−SR)×100

ER: average count (cpm) of experiment group

SR: average count (cpm) target cell cultured in culture medium

MR: average count (cpm) of target cell treated with 5% Triton X-100.

The experimental results were shown in Table 5. LAK cells showed cell lysis increase by 8 times in comparison with non-immune cells, and by 1.5 times in comparison with BCG injection group. MBT-2 cell line showed cell lysis increase by 5 times in comparison with non-immune cells. These results represent possibility of CIA for anti-cancer treatments instead of BCG resulting in various side effects.

TABLE 5

| | Injection days | | | |
|---|---|---|---|---|
| | 0 | 3 | 7 | 15 |
| Sarcoma 180 | | | | |
| Control group | 100 | 100 | 100 | 100 |
| BCG | 92 ± 4 | 110 ± 2 | 632 ± 13 | 189 ± 4 |
| CIA07 | 94 ± 7 | 154 ± 3 | 802 ± 10 | 109 ± 7 |
| MBT-2 | | | | |
| Control group | 100 | 100 | 100 | 100 |
| BCG | 103 ± 3 | 96 ± 7 | 402 ± 11 | 98 ± 3 |
| CIA07 | 97 ± 4 | 121 ± 9 | 513 ± 13 | 109 ± 6 |

Figure 12:
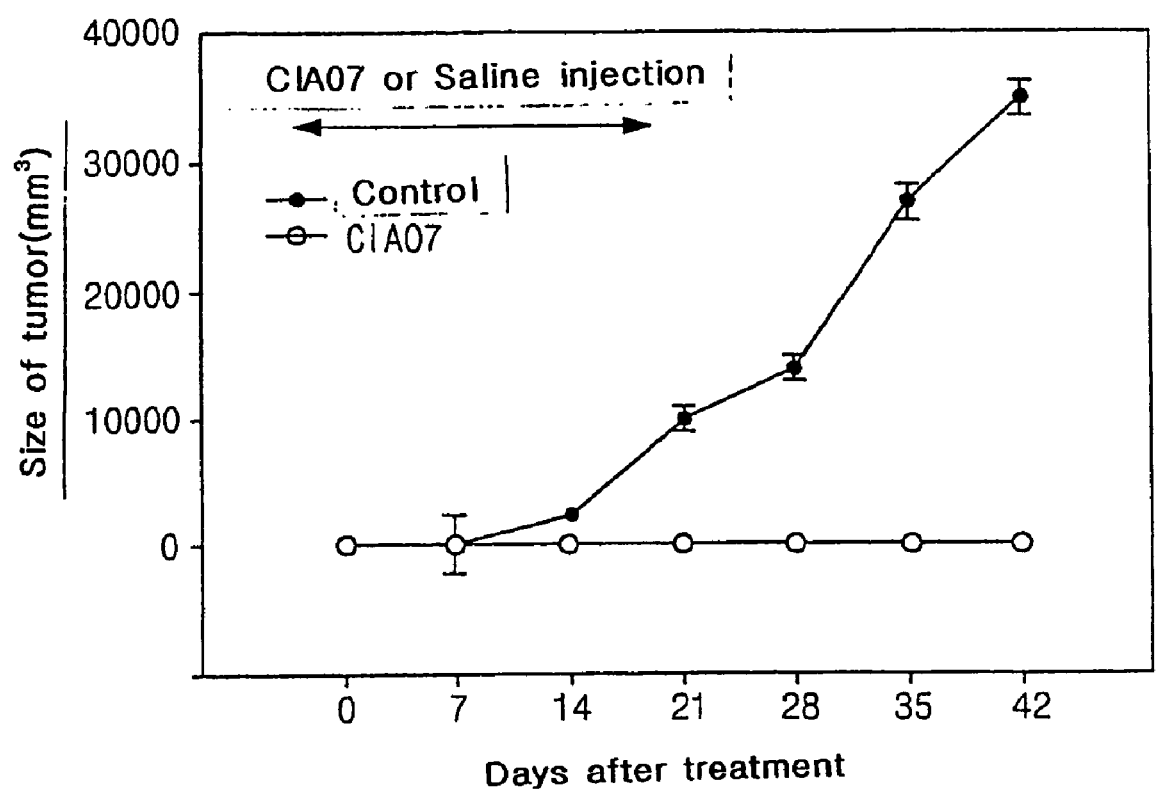
FIG. 12 is a graph illustrating inhibition of cancer growth when *E. coli* derived anti-cancer treatment CIA07 is administrated in C3H/HeJ mouse to which mouse bladder cancer cell line (MBT2) was transplanted.

Experiment for identifying anti-cancer activity in mouse $5\times10^5$ MBT2 cells (C3H/He derived bladder cancer cell) were subcutaneously injected at two positions (left, shoulder, right thigh) of a 5~8 week old male C3H/HeJ mouse. Here, several pricks for injection should be avoided in order to generate single cancer tissue. The used mice were 6 to 10 per an experimental group. From the next day after injecting tumor cell, 100 ul of CIA07 (50 ug of CIA02+500 ng of CIA05) or physiological salt solution was injected in cell line injected position one time everyday for 1 week and every two days for the next 2 weeks. The size of cancer generated in the hypoderm was measured three times per a week using caliper. The results were shown in FIG. 12. It was shown that the growth of cancer tissue was inhibited in CIA05 injection group in comparison with physiological salt solution injection group.

INDUSTRIAL APPLICABILITY

The anti-cancer treatment CIA07 of mixing two *E. coli* derived materials CIA02 and CIA05 according to the present invention has higher safety than the conventional treatment and minimizes production cost due to simplicity of production process. Also, CIA07 induces more effective and specific immunization due to mixing the two materials. Additionally, the present invention is cheaper than CpG due to physical process of DNA and more effective than BCG.

Accordingly, the *E. coli* derived anti-cancer treatment CIA07 according to the present invention is more significant in industrial application for anti-cancer treatment and immune adjuvant.

What is claimed is:

1. A composition comprising:
   a) bacterial DNA fragments; and
   b) *Escherichia Coli* (*E. coli*) lipopolysaccharide having a molecular weight of about 3,000 to about 10,000 daltons, wherein said *E. Coli* lipopolysaccharide comprises a core antigen, but not an O-antigen.

2. The composition of claim 1, wherein said bacterial DNA fragments comprise unmethylated CpG sequence.

3. The composition of claim 1, wherein said bacterial DNA fragments are 0.5 to 2.0 kb.

4. The composition of claim 1, wherein the weight ratio of a) and b) ranges from 500:1 to 1:500.

5. The composition of claim 1, wherein a) and b) are mixed by shaking.

6. The composition of claim 1, wherein said *E. coli* lipopolysaccharide has a structure as produced from *E. coli* strain EG0021 (KCCM-1 0374).

7. The composition of claim 1, wherein said composition induces a T helper type 1 immune response.

8. The composition according to claim 1, wherein said *E. coli* lipopolysaccharide is detoxified with alkali treatment.

9. The composition according to claim 1, wherein said *E. coli* lipopolysaccharide is produced by alkali treatment of lipopolysaccharide from *E. coli* strain EG0021 (KCCM-10374).

10. A method for producing an immune-stimulating composition, comprising: combining bacterial DNA fragments with non-toxic lipopolysaccharides, wherein said fragments and said non-toxic lipopolysaccharides are combined in a ratio of from about 500:1 to about 1:500 by weight, wherein said lipopolysaccharides are *E. Coli* strain EG0021 (KCCM 10374).

11. A method of stimulating the immune system of a mammal, comprising administering the composition of claim 1 to the mammal in an amount effective to stimulate the immune system of said mammal.

* * * * *

UNITED STATES PATENT AND TRADEMARK OFFICE
CERTIFICATE OF CORRECTION

PATENT NO. : 7,507,802 B2 Page 1 of 1
APPLICATION NO. : 10/515353
DATED : March 24, 2009
INVENTOR(S) : Bo-Young Ahn et al.

It is certified that error appears in the above-identified patent and that said Letters Patent is hereby corrected as shown below:

Title page, item (73) Assignee(s) should read: -- EYEGENE, INC., Seoul (KR), and DAEWOONG CO., LTD., Seoul (KR) --

Signed and Sealed this

Thirtieth Day of March, 2010

David J. Kappos
*Director of the United States Patent and Trademark Office*